United States Patent
Coats et al.

(10) Patent No.: US 11,938,102 B2
(45) Date of Patent: *Mar. 26, 2024

(54) S-ENANTIOMERICALLY ENRICHED COMPOSITIONS OF BETA BLOCKERS FOR TREATING AMYOTROPHIC LATERAL SCLEROSIS

(71) Applicant: ACTIMED THERAPEUTICS LIMITED, Ascot (GB)

(72) Inventors: Andrew J. S. Coats, St. Kilda (AU); Stefan Anker, Berlin (DE); Jochen Springer, Falkensee (DE)

(73) Assignee: ACTIMED THERAPEUTICS LIMITED, Ascot (GB)

( * ) Notice: Subject to any disclaimer, the term of this patent is extended or adjusted under 35 U.S.C. 154(b) by 307 days.

This patent is subject to a terminal disclaimer.

(21) Appl. No.: 17/231,789

(22) Filed: Apr. 15, 2021

(65) Prior Publication Data

US 2021/0330615 A1 Oct. 28, 2021

Related U.S. Application Data

(63) Continuation of application No. 16/657,018, filed on Oct. 18, 2019, now Pat. No. 11,007,158, which is a continuation of application No. 14/776,037, filed as application No. PCT/AU2014/000274 on Mar. 14, 2014, now Pat. No. 10,449,166.

(60) Provisional application No. 61/786,235, filed on Mar. 14, 2013.

(51) Int. Cl.
*A61K 31/138* (2006.01)

(52) U.S. Cl.
CPC ................... *A61K 31/138* (2013.01)

(58) Field of Classification Search
CPC .................................................. A61K 31/138
See application file for complete search history.

(56) References Cited

U.S. PATENT DOCUMENTS

| 2007/0021421 A1 | 1/2007 | Hampton |
| 2012/0095070 A1 | 4/2012 | Springer et al. |

FOREIGN PATENT DOCUMENTS

| WO | 2010125348 A1 | 11/2010 |
| WO | 2014/016585 A1 | 1/2014 |

OTHER PUBLICATIONS

Aleksander Radunovic et al., "Clinical care of patients with amyotrophic lateral sclerosis", The Lancet Neurology, pp. 913-925, vol. 6, No. 10, published on Oct. 6, 2007.
Bensimon, G. et al., "A study of riluzole in the treatment of advanced stage or elderly patients with amyotrophic lateral sclerosis", Journal of Neurology, pp. 609-615, vol. 249, No. 5, published May 2002.
Rubika Balendra et al., "Use of clinical staging in amyotrophic lateral sclerosis for hase 3 clinical trials", Journal of Neurology, Neurosurgery, and Psychiatry, pp. 45-49, vol. 86, No. 1, published on Jan. 24, 2014.
Jose C. Roche et al.,"A proposed staging system for amyotrophic lateral sclerosis", A Journal of Neurology, pp. 847-852, vol. 135, No. 3, published on Jan. 23, 2012.
Bensimon, G. et al., "A Controlled Trial of Riluzole in Amyotrophic Lateral Sclerosis", The New England Journal of Medicine, pp. 585-591, vol. 330, No. 9, Published on Mar. 3, 1994.
Kenley, R.A. et al., "Formolerol fumarate and roxithromycin effects on muscle mass in an animal model of cancer cachexia", Oncology Reports, pp. 1113-1121, vol. 19, published on May 1, 2008.
International Search Report of PCT/AU2014/000274 dated May 13, 2014 (Authorized Officer, Grant McNeice).
Martinez-Gomez, M.A. et al., "Chiral separation of oxprenolol by affinity electrokinetic chromatography-partial filling technique using human serum albumin as chiral selector", Journal of Pharmaceutical and Biomedical Analysis, pp. 76-81, vol. 39, Nos. 1-2, published Sep. 1, 2005.
Dong et al., "Pharmacokinetics of Chiral Drugs", Chiral Dugs: Chemistry and Biological Action, 2011, First Edition, pp. 347-379.

*Primary Examiner* — Shobha Kantamneni
(74) *Attorney, Agent, or Firm* — MH2 TECHNOLOGY LAW GROUP, LLP

(57) ABSTRACT

The present invention relates to S-enantiomerically enriched compositions of beta blockers and uses thereof, including uses of the beta blocker compositions for treating amyotrophic lateral sclerosis. The beta blocker compositions can also be used for preventing loss of lean mass, preventing body weight loss in subjects, improving quality of life in subjects, and prolonging survival in amyotrophic lateral sclerosis patients. The beta blocker can be oxprenolol or a pharmaceutically acceptable salt thereof.

13 Claims, 21 Drawing Sheets

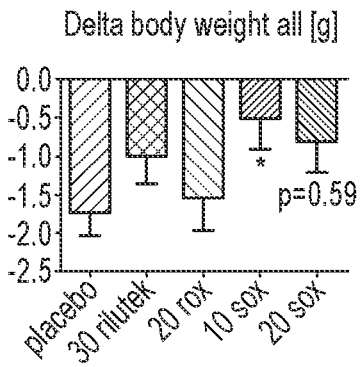

Fig 20(A)
Delta body weight all [g]

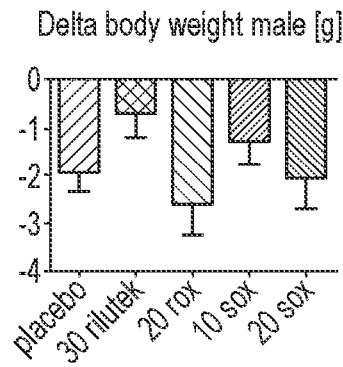

Fig 20(B)
Delta body weight male [g]

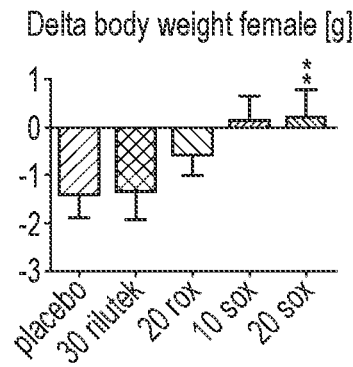

Fig 20(C)
Delta body weight female [g]

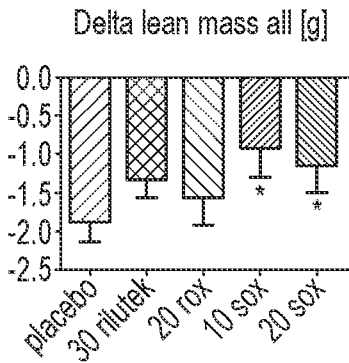

Fig 20(D)
Delta lean mass all [g]

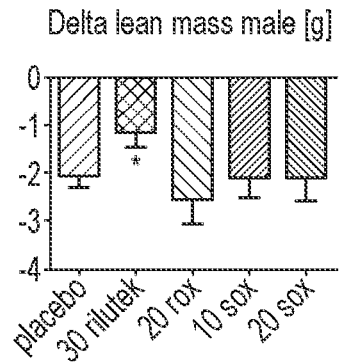

Fig 20(E)
Delta lean mass male [g]

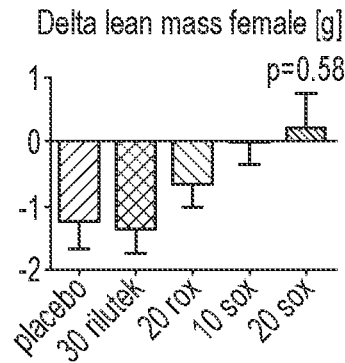

Fig 20(F)
Delta lean mass female [g]

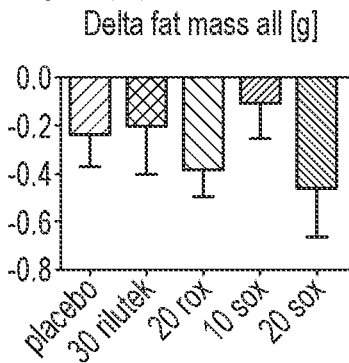

Fig 20(G)
Delta fat mass all [g]

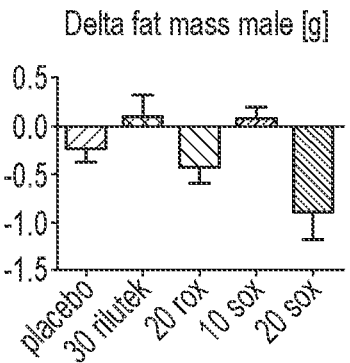

Fig 20(H)
Delta fat mass male [g]

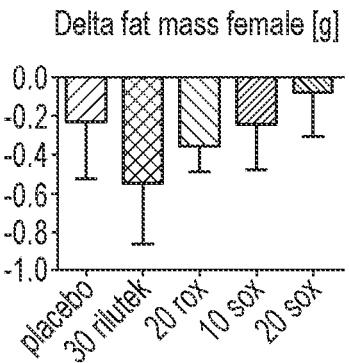

Fig 20(I)
Delta fat mass female [g]

*: $p<0.5$ vs placebo
: $p<0.05$ vs rilutek

| | |
|---|---|
| placebo: | n=21 |
| 30 mg/kg/d rilutek: | n=24 |
| 20 mg/kg/d r-oxprenolol: | n=29 |
| 10 mg/kg/d s-oxprenolol: | n=16 |
| 20 mg/kg/d s-oxprenolol: | n=26 |

| | |
|---|---|
| placebo: | n=14 |
| 30 mg/kg/d rilutek: | n=13 |
| 20 mg/kg/d r-oxprenolol: | n=14 |
| 10 mg/kg/d s-oxprenolol: | n=7 |
| 20 mg/kg/d s-oxprenolol: | n=12 |

| | |
|---|---|
| placebo: | n=8 |
| 30 mg/kg/d rilutek: | n=11 |
| 20 mg/kg/d r-oxprenolol: | n=15 |
| 10 mg/kg/d s-oxprenolol: | n=9 |
| 20 mg/kg/d s-oxprenolol: | n=14 |

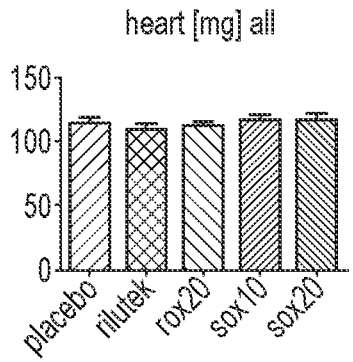

Fig 21(A) heart [mg] all

Fig 21(B) heart [mg] male

Fig 21(C) heart weight [mg] female

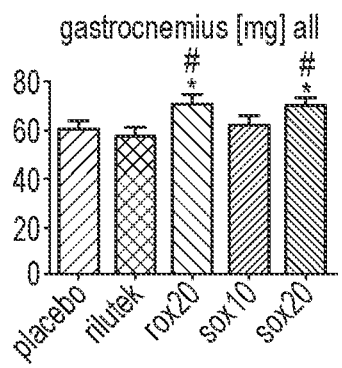

Fig 21(D) gastrocnemius [mg] all

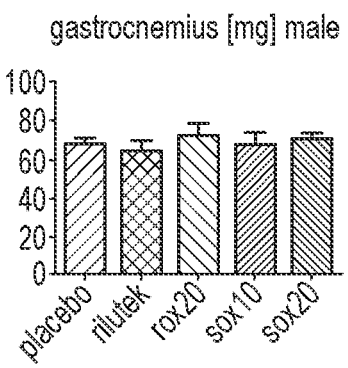

Fig 21(E) gastrocnemius [mg] male

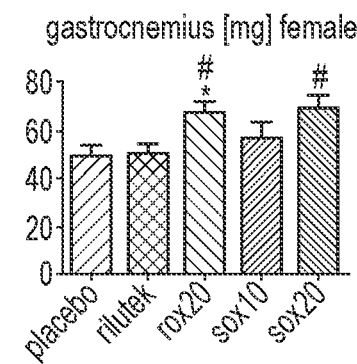

Fig 21(F) gastrocnemius [mg] female

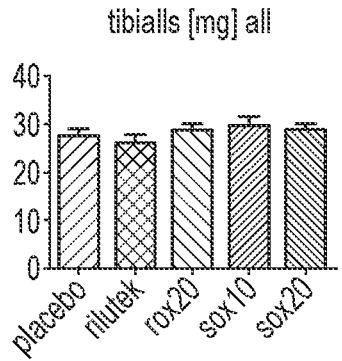

Fig 21(G) tibialis [mg] all

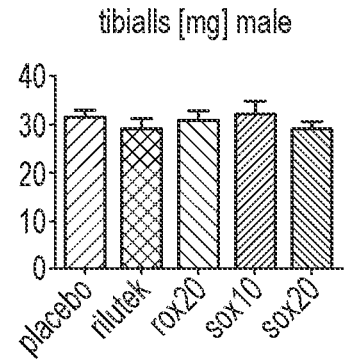

Fig 21(H) tibialis [mg] male

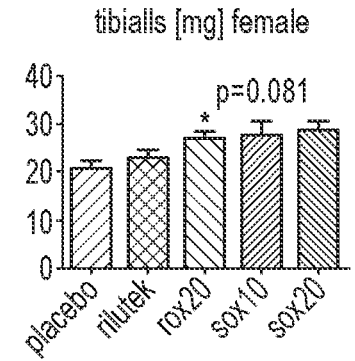

Fig 21(I) tibialis [mg] female

*: $p<0.5$ vs placebo  ##: $p<0.01$ vs rilutek
: $p<0.05$ vs rilutek  S: $p<0.05$ vs rox 20

| | | | | |
|---|---|---|---|---|
| placebo: | n=21 | placebo: | n=14 | placebo: | n=8 |
| 30 mg/kg/d rilutek: | n=24 | 30 mg/kg/d rilutek: | n=13 | 30 mg/kg/d rilutek: | n=11 |
| 20 mg/kg/d r-oxprenolol: | n=29 | 20 mg/kg/d r-oxprenolol: | n=14 | 20 mg/kg/d r-oxprenolol: | n=15 |
| 10 mg/kg/d s-oxprenolol: | n=16 | 10 mg/kg/d s-oxprenolol: | n=7 | 10 mg/kg/d s-oxprenolol: | n=9 |
| 20 mg/kg/d s-oxprenolol: | n=26 | 20 mg/kg/d s-oxprenolol: | n=12 | 20 mg/kg/d s-oxprenolol: | n=14 |

S-ENANTIOMERICALLY ENRICHED COMPOSITIONS OF BETA BLOCKERS FOR TREATING AMYOTROPHIC LATERAL SCLEROSIS

CROSS-REFERENCE TO RELATED APPLICATIONS

This application is a Continuation of U.S. application Ser. No. 16/657,018, filed Oct. 18, 2019 (Allowed), which is a Continuation of U.S. application Ser. No. 14/776,037, filed Sep. 14, 2015 (now U.S. Pat. No. 10,449,166), which is a U.S. National Stage Application of PCT/AU2014/000274, filed Mar. 14, 2014, which claims the priority benefit of U.S. Provisional Patent Application Ser. No. 61/786,235, filed Mar. 14, 2013, which is incorporated herein by reference in its entirety.

TECHNICAL FIELD

The present invention relates to S-enantiomerically enriched compositions of beta blockers or pharmaceutically acceptable salts thereof and uses thereof, including uses of the beta blocker compositions for treating amyotrophic lateral sclerosis. The beta blocker can be oxprenolol or a pharmaceutically acceptable salt thereof.

BACKGROUND

Amyotrophic lateral sclerosis (ALS) covers a spectrum of neurodegenerative syndromes characterized by progressive muscular paralysis reflecting degeneration of motor neurons in the brain and spinal cord. ALS is one of the most common neurodegenerative disorders, with an incidence of 1 to 2 per 100,000 and a prevalence of 4 to 6 per 100,000; as many as 30,000 Americans have the disease at any given time (Worms P M. The epidemiology of motor neuron disease: a review of recent studies. J Neurol Sci 2001, 191 :3-9). The incidence in males is higher than in females (1.6:1). 5-10% of patients have a positive family history of ALS, most commonly with an autosomal dominant inheritance pattern. ALS is a disease of mature adults, with a median age of onset of 55 years and its frequency increases with age until age 75. Overall 50% of patients die within the first three years since the first clinical manifestations. Apart from age or a positive family history, a number of factors and enviromnental toxins have been further studied as risk factors. A high relative risk was described in smokers, soccer players, especially Italians and veterans of the Gulf War.

Oxprenolol is a non-selective beta blocker which possesses some intrinsic sympathomimetic activity. Because of its beta blocker function, oxprenolol has been used for the treatment of various diseases such as angina pectoris, abnormal heart rhythms, and high blood pressure. Oxprenolol is lipophilic and crosses the blood-brain barrier more easily than other more water soluble beta blockers. As a result, oxprenolol is associated with a higher incidence of CNS-related side effects than other beta blockers, but also has more central CNS modes of action.

The disclosure of all publications, patents, patent applications, and published patent applications referred to herein are hereby incorporated herein by reference in their entirety.

BRIEF SUMMARY OF THE INVENTION

The present invention relates to S-enantiomerically enriched compositions of beta blockers or pharmaceutically acceptable salts thereof and uses thereof, including uses of the beta blocker compositions for treating amyotrophic lateral sclerosis. The beta blocker can be oxprenolol or a pharmaceutically acceptable salt thereof.

The present disclosure provides, in some embodiments, a method of treating amyotrophic lateral sclerosis in an individual having amyotrophic lateral sclerosis, comprising administering to the individual an effective amount of a composition comprising a beta blocker or a pharmaceutically acceptable salt thereof, wherein beta blocker has one chiral center and the composition is enantiomerically enriched for the S-enantiomer.

The present disclosure provides, in some embodiments, a method of prolonging survival of an individual having amyotrophic lateral sclerosis, comprising administering to the individual an effective amount of a composition comprising a beta blocker or a pharmaceutically acceptable salt thereof, wherein beta blocker has one chiral center and the composition is enantiomerically enriched for the S-enantiomer.

The present disclosure provides, in some embodiments, a method of delaying the development of amyotrophic lateral sclerosis in an individual having amyotrophic lateral sclerosis, comprising administering to the individual an effective amount of a composition comprising a beta blocker or a pharmaceutically acceptable salt thereof, wherein beta blocker has one chiral center and the composition is enantiomerically enriched for the S-enantiomer.

The present disclosure provides, in some embodiments, a method of preventing loss of lean mass of an individual having amyotrophic lateral sclerosis, comprising administering to the individual an effective amount of a composition comprising a beta blocker or a pharmaceutically acceptable salt thereof, wherein beta blocker has one chiral center and the composition is enantiomerically enriched for the S-enantiomer.

The present disclosure provides, in some embodiments, a method of preventing muscle wasting of an individual having amyotrophic lateral sclerosis, comprising administering to the individual an effective amount of a composition comprising a beta blocker or a pharmaceutically acceptable salt thereof, wherein beta blocker has one chiral center and the composition is enantiomerically enriched for the S-enantiomer.

The present disclosure provides, in some embodiments, a method of improving quality of life in an individual having amyotrophic lateral sclerosis, comprising administering to the individual an effective amount of a composition comprising a beta blocker or a pharmaceutically acceptable salt thereof, wherein beta blocker has one chiral center and the composition is enantiomerically enriched for the S-enantiomer.

In some embodiments, the beta blocker is oxprenolol or a pharmaceutically acceptable salt thereof. In some embodiments, the beta blocker is oxprenolol or a pharmaceutically acceptable salt thereof, wherein the composition is enantiomerically enriched for S-oxprenolol. In some embodiments, the composition comprises an enantiomeric excess of at least about 50% of S-oxprenolol. In some embodiments, the composition comprises an enantiomeric excess of at least about 80% of S-oxprenolol. In some embodiments, the composition comprises an enantiomeric excess of at least about 99% of S-oxprenolol. In some embodiments, the composition comprises an enantiomeric excess of at least 99.9% of S-oxprenolol. In some embodiments, the amyotrophic lateral sclerosis is sporadic amyotrophic lateral sclerosis. In some embodiments, the amyotrophic lateral sclerosis is familial amyotrophic lateral sclerosis. In some embodiments, the amyotrophic lateral sclerosis is Western Pacific amyotrophic lateral sclerosis. In some embodiments, the amyotrophic lateral sclerosis is juvenile amyotrophic lateral sclerosis. In some embodiments, the amyotrophic lateral sclerosis is Hiramaya Disease. In some embodiments, the amyotrophic lateral sclerosis is progressive bulbar palsy (PBP), progressive muscular atrophy (PMA), primary lateral sclerosis (PLS), or ALS with multi-system involvement. In some embodiments, the composition is administered orally. In some embodiments, the amount of S-oxprenolol in the composition is about 80 to about 160 mg daily. In some embodiments, the composition is administered daily or twice daily.

The present disclosure provides, in some embodiments, a kit comprising a pharmaceutical composition comprising a composition comprising a beta blocker or a pharmaceutically acceptable salt thereof, wherein beta blocker has one chiral center and the composition is enantiomerically enriched for the S-enantiomer; and a pharmaceutically acceptable carrier for treating amyotrophic lateral sclerosis. In some embodiments, the beta blocker is oxprenolol.

BRIEF DESCRIPTION OF THE FIGURES

FIG. 20A is a graph showing the change in body weight of mice populations that were administered with S-oxprenolol, R-oxprenolol, or rilutek. FIG. 20B is a graph showing the change in body weight of male mice populations that were administered with S-oxprenolol R-oxprenolol, or rilutek. FIG. 20C is a graph showing the change in body weight of female mice populations that were administered with S-oxprenolol, R-oxprenolol., or rilutek. FIG. 20D is a graph showing the change in lean mass of mice populations that were administered with S-oxprenolol., R-oxprenolol, or rilutek. FIG. 20E is a graph showing the change in lean mass of male mice populations that were administered with S-oxprenolol, R-oxprenolol, or rilutek. FIG. 20F is a graph showing the change in lean mass of female mice populations that were administered with S-oxprenolol, R-oxprenolol, or rilutek. FIG. 20G is a graph showing the change in fat mass of mice populations that were administered with S-oxprenolol, R-oxprenolol, or rilutek. FIG. 20H is a graph showing the change in fat mass of male mice populations that were administered with S-oxprenolol, R-oxprenolol, or rilutek. FIG. 20I is a graph showing the change in fat mass of female mice populations that were administered with S-oxprenolol, R-oxprenolol, or rilutek. The sample size in the population is indicated by "n."

FIG. 21A is a graph showing the heart mass of mice populations that were administered with S-oxprenolol, R-oxprenolol, or rilutek at the end of the study. FIG. 21B is a graph showing the heart mass of male mice populations that were administered with S-oxprenolol, R-oxprenolol, or rilutek at the end of the study. FIG. 21C is a graph showing the heart mass of female mice populations that were administered with S-oxprenolol, R-oxprenolol, or rilutek at the end of the study. FIG. 21D is a graph showing gastrocnemius muscle weight of mice populations that were administered with S-oxprenolol, R-oxprenolol, or rilutek at the end of the study. FIG. 21E is a graph showing gastrocnemius muscle weight of male mice populations that were administered with S-oxprenolol, R-oxprenolol, or rilutek at the end of the study. FIG. 21F is a graph showing gastrocnemius muscle weight of female mice populations that were administered with S-oxprenolol, R-oxprenolol, or rilutek at the end of the study. FIG. 21G is a graph showing tibialis muscle weight of mice populations that were administered with S-oxprenolol, R-oxprenolol, or rilutek at the end of the study. FIG. 21H is a graph showing tibialis muscle weight of male mice populations that were administered with S-oxprenolol, R-oxprenolol, or rilutek at the end of the study. FIG. 21I is a graph showing tibialis muscle weight of female mice populations that were administered with S-oxprenolol, R-oxprenolol, or rilutek at the end of the study. The sample size in the population is indicated by "n."

DETAILED DESCRIPTION OF THE INVENTION

Figure 1:
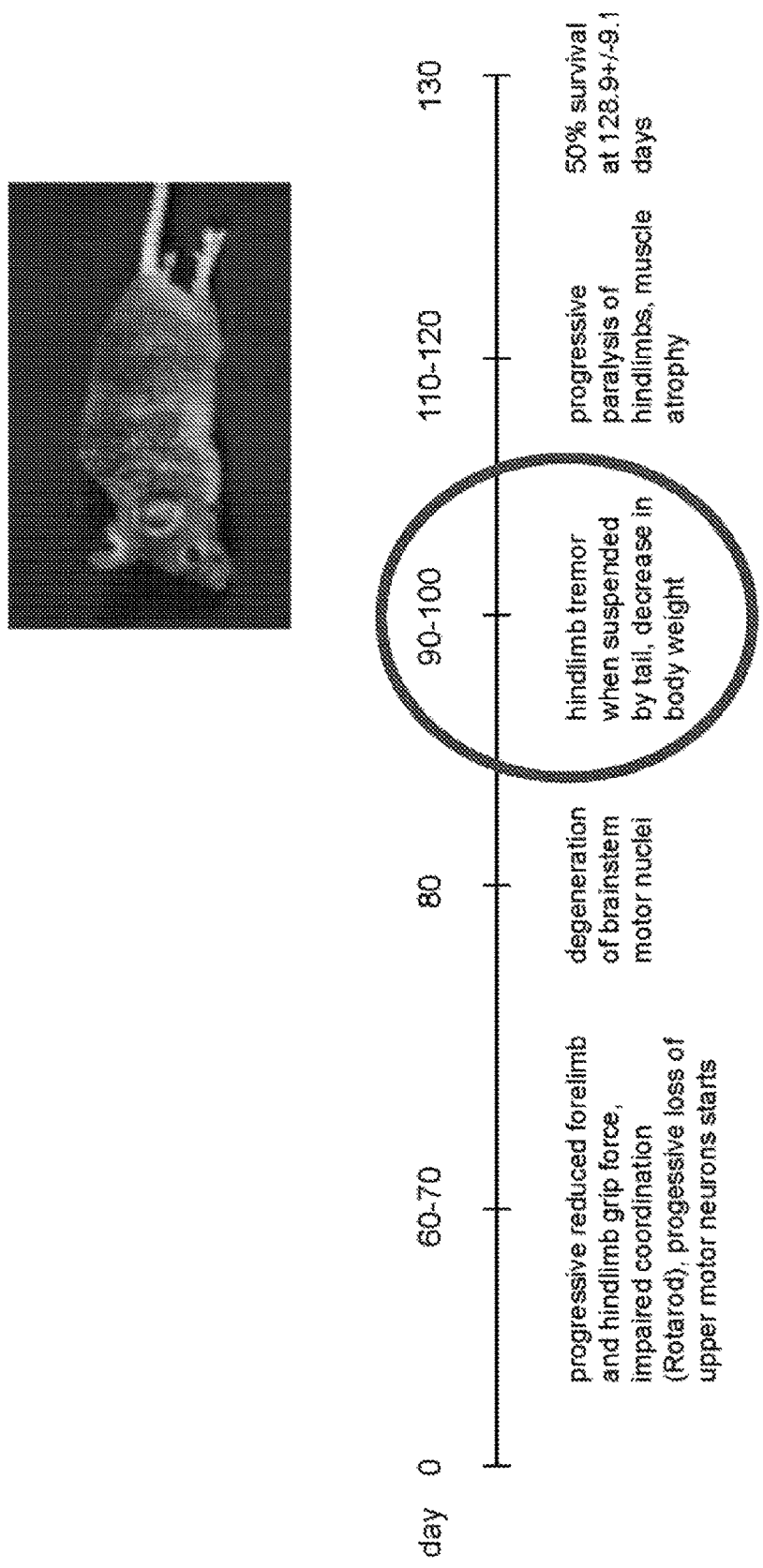
FIG. 1 is a diagram showing a clinical symptomatological evaluation of the B6SJL-Tg(SOD1*G93A)1Gur/J ALS transgenic mouse.

The present invention provides use of an S-enantiomerically enriched composition of a beta blocker for achieving beneficial results in individuals having amyotrophic lateral sclerosis, such as treating amyotrophic lateral sclerosis, prolonging survival, preventing lean mass loss, improving quality of life, and/or treating muscle wasting. In an S-enantiomerically enriched composition of a beta blocker or a pharmaceutically acceptable salt thereof the beta blocker or a pharmaceutically acceptable salt thereof has one chiral center and the composition is enantiomerically enriched for the S-enantiomer. Thus, as used herein, "S-enantiomerically enriched composition of a beta blocker" refers to a beta blocker having one chiral center and the composition is enantiomerically enriched for the S-enantiomer. In some embodiments, the beta blocker is oxprenolol or a pharmaceutically acceptable salt thereof.

The present invention is based on the surprising finding that S-oxprenolol significantly improved survival in animals having amyotrophic lateral sclerosis in an experiment using an amyotrophic lateral sclerosis animal model. Other effects of the compositions were observed on preserving lean body mass and preventing body weight loss in the animals. At least, these effects suggest that S-oxprenolol is effective in treating amyotrophic lateral sclerosis and prolonging survival.

Thus, the present invention, in one aspect, provides methods of treating amyotrophic lateral sclerosis, prolonging survival, preventing lean mass loss, preventing and/or treating muscle wasting, or improving quality of life in an individual having amyotrophic lateral sclerosis, comprising administering to the individual an effective amount of an S-enantiomerically enriched composition of a beta blocker or a pharmaceutically acceptable salt thereof. In some embodiments, the beta blocker is oxprenolol or a pharmaceutically acceptable salt thereof.

Also provided are kits, unit dosages, medicines, and articles of manufacture that are useful for methods described herein.

Definitions

The following terms have the following meanings unless otherwise indicated. Any undefined terms have their art recognized meanings.

As used herein, "treatment" or "treating" is an approach :for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of amyotrophic lateral sclerosis. The methods of the invention contemplate any one or more of these aspects of treatment.

The term "individual" refers to a mammal and includes, but is not limited to, human, bovine, horse, feline, canine, rodent, or primate. In some embodiments, the individual is a human.

As used herein, an "at risk" individual is an individual who is at risk of developing amyotrophic lateral sclerosis. An individual "at risk" may or may not have detectable disease, and may or may not have displayed detectable disease prior to the treatment methods described herein. "At risk" denotes that an individual has one or more so-called risk factors, which are measurable parameters that correlate with development of amyotrophic lateral sclerosis. An individual having one or more of these risk factors has a higher probability of developing amyotrophic lateral sclerosis than an individual without these risk factor(s).

As used herein, "delaying" the development of a disease means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of a disease is a method that reduces probability of disease development in a given time frame and/or reduces the extent of the disease in a given time frame, when compared to not using the method. Such comparisons are typically based on clinical studies, using a statistically significant number of subjects.

As used herein, by "combination therapy" is meant that a first agent be administered in conjunction with another agent. "In conjunction with" refers to administration of one treatment modality in addition to another treatment modality, such as administration of a nanoparticle composition described herein in addition to administration of the other agent to the same individual. As such, "in conjunction with" refers to administration of one treatment modality before, during, or after delivery of the other treatment modality to the individual. Such combinations are considered to be part of a single treatment regimen or regime.

The term "effective amount" used herein refers to an amount of a compound or composition sufficient to treat a specified disorder, condition or disease such as ameliorate, palliate, lessen, and/or delay one or more of its symptoms. In reference to amyotrophic lateral sclerosis, an effective amount comprises an amount sufficient to prevent or delay other unwanted symptoms associated with amyotrophic lateral sclerosis. In some embodiments, an effective amount is an amount sufficient to delay development. In some embodiments, an effective amount is an amount sufficient to prevent or delay recurrence. An effective amount can be administered in one or more administrations.

The term "simultaneous administration," as used herein, means that a first therapy and second therapy in a combination therapy are administered with a time separation of no more than about 15 minutes, such as no more than about any of 10, 5, or 1 minutes. When the first and second therapies are administered simultaneously, the first and second therapies may be contained in the same composition (e.g., a composition comprising both a first and second therapy) or in separate compositions (e.g., a first therapy in one composition and a second therapy is contained in another composition).

As used herein, the term "sequential administration" means that the first therapy and second therapy in a combination therapy are administered with a time separation of more than about 15 minutes, such as more than about any of 20, 30, 40, 50, 60, or more minutes. Either the first therapy or the second therapy may be administered first. The first and second therapies are contained in separate compositions, which may be contained in the same or different packages or kits.

As used herein, the term "concurrent administration" means that the administration of the first therapy and that of a second therapy in a combination therapy overlap with each other.

As used herein, by "pharmaceutically acceptable" or "pharmacologically compatible" is meant a material that is not biologically or otherwise undesirable, e.g., the material may be incorporated into a pharmaceutical composition administered to an individual without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

An "adverse event" or "AE" as used herein refers to any untoward medical occurrence in an individual receiving a marketed pharmaceutical product or in an individual who is participating on a clinical trial who is receiving an investigational or non-investigational pharmaceutical agent.

The term "isomers" or "stereoisomers" refers to compounds which have identical chemical constitution, but differ with regard to the arrangement of the atoms or groups in space.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "enantiomerically enriched" means that the racemic mixture (i.e., 50/50 mixture of the enantiomers) has been purified such that one enantiomer comprises greater than 50% of the total amount of the compound present. For example, a composition that is enantiomerically enriched for S-oxprenolol is a composition wherein more than 50% of the oxprenolol is the S-enantiomer of oxprenolol (S-oxprenolol).

The degree of enantiomeric enrichment of a composition can be determined by "enantiomeric excess," or ee. "Enantiomeric excess" represents the percentage of one enantiomer in excess of the other. For instance, a composition having a 75:25 mixture of S-oxprenolol and R-oxprenolol has a 75−25=50% ee, while a 50:50 racemic mixture has a 50−50=0% ee. The value of ee will be a number from 0 to 100, 0 being racemic and 100 being pure, single enantiomer.

The term "pharmaceutically acceptable salt" means a salt which is acceptable for administration to a subject, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to the subject. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

It will be appreciated that the term "or a salt or solvate thereof" is intended to include all permutations of salts and solvates, such as a solvate of a pharmaceutically acceptable salt of a subject compound.

As used herein, "in conjunction with" refers to administration of one treatment modality in addition to another treatment modality. As such, "in conjunction with" refers to administration of one treatment modality before, during or after administration of the other treatment modality to the individual.

As used herein and in the appended claims, the singular forms "a," "an," and "the" include plural reference unless the context clearly indicates otherwise.

Reference to "about" a value or parameter herein includes (and describes) embodiments that are directed to that value or parameter per se. For example, description referring to "about X" includes description of "X."

It is understood that aspects and variations of the invention described herein include "consisting" and/or "consisting essentially at" aspects and variations.

Methods of the Present Invention

The present disclosure, in one aspect, provides methods of treating amyotrophic lateral sclerosis. In some embodiments, there is provided a method of treating amyotrophic lateral sclerosis in an individual having amyotrophic lateral sclerosis, comprising administering to the individual an effective amount of an S-enantiomerically enriched composition of a beta blocker or a pharmaceutically acceptable salt thereof (such as a composition having at least about any one of 10%, 20%, 30%, 40%, 50%, 60%, 70%, 80%, 90%, 95%, 96%, 97%, 98%, 99%, or 99.9% ee). In some embodiments, the beta blocker is selected from the group consisting of acebutolol, atenolol, betaxolol, bisoprolol, carteolol, celeprolol, labetalol, metoprolol, nadolol, nehivolol, oxprenolol, penbutolol, pindolol, propanolol, sotalol, esmolol, carvedilol, timolol, bopindolol, medroxalol, bucindolol, levobunolol, metipranolol, celiprolol and propafenone or a pharmaceutically acceptable salt thereof. In some embodiments, the beta blocker is oxprenolol or a pharmaceutically acceptable salt thereof. In some embodiments, the composition comprises an enantiomeric excess of at least about 10% (such as at least about any one of 20%, 30%, 40%, 50%, 60%, 70%, 80%, 90%, 95%, 96%, 97%, 98%, 99%, or 99.9%) of S-oxprenolol. In some embodiments, there is provided a method of treating amyotrophic lateral sclerosis in an individual having amyotrophic lateral sclerosis, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of treating amyotrophic lateral sclerosis in an individual having amyotrophic lateral sclerosis, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg).

In some embodiments, there is provided a method of prolonging survival of an individual having amyotrophic lateral sclerosis, comprising administering to the individual an effective amount of an S-enantiomerically enriched composition of a beta blocker or a pharmaceutically acceptable salt thereof (such as a composition having at least about any one of 10%, 20%, 30%, 40%, 50%, 60%, 70%, 80%, 90%, 95%, 96%, 97%, 98%, 99%, or 99.9% ee). In some embodiments, the beta blocker is selected from the group consisting of acebutolol, atenolol, betaxolol, bisoprolol, carteolol, celeprolol, labetalol, metoprolol, nadolol, nebivolol, oxprenolol, penbutolol, pindolol, propanolol, sotalol, esmolol, carvedilol, timolol, bopindolol, medroxalol, bucindolol, levobunolol, metipranolol, celiprolol and propafenone. In some embodiments, the beta Mocker is oxprenolol or a pharmaceutically acceptable salt thereof. In some embodiments, the composition comprises an enantiomeric excess of at least about 10% (such as at least about any one of 20%, 30%, 40%, 50%, 60%, 70%, 80%, 90%, 95%, 96%, 97%, 98%, 99%, or 99.9%) of S-oxprenolol. In some embodiments, there is provided a method of prolonging survival in an individual having amyotrophic lateral sclerosis, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of prolonging survival of an individual having amyotrophic lateral sclerosis, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the method prolongs the survival of the individual by at least any of 1, 2, 3, 4, 5, 6, 7. 8.9, 10, 11, 12, 18, or 24 months.

In some embodiments, there is provided a method of prolonging progression-free survival in an individual with amyotrophic lateral sclerosis, comprising administering to the individual an effective amount of an S-enantiomerically enriched composition of a beta blocker or a pharmaceutically acceptable salt thereof (such as a composition having at least about any one of 10%, 20%, 30%, 40%, 50%, 60%, 70%, 80%, 90%, 95%, 96%, 97%, 98%, 99%, or 99.9% ee). In some embodiments, the beta blocker is selected from the group consisting of acebutolol, atenolol, betaxolol, bisoprolol, carteolol, celeprolol, labetalol, metoprolol, nadolol, nebivolol, oxprenolol, penbutolol, pindolol, propanolol, sotalol, esmolol, carvedilol, timolol, bopindolol, medroxalol, bucindolol, levobunolol, metipranolol, celiprolol and propafenone. In some embodiments, the beta blocker is oxprenolol or a pharmaceutically acceptable salt thereof. In some embodiments, the composition comprises an enantiomeric excess of at least about 10% (such as at least about any one of 20%, 30%, 40%, 50%, 60%, 70%, 80%, 90%, 95%, 96%, 97%, 98%, 99%, or 99.9%) of S-oxprenolol. In some embodiments, there is provided a method of prolonging progression-free survival in an individual with amyotrophic lateral sclerosis, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of prolonging progression-free survival in an individual with amyotrophic lateral sclerosis, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg).

In some embodiments, there is provided a method of alleviating one or more symptoms associated with amyotrophic lateral sclerosis, comprising administering to the individual an effective amount of an S-enantiomerically enriched composition of a beta blocker or a pharmaceutically acceptable salt thereof (such as a composition having at least about any one of 10%, 20%, 30%, 40%, 50%, 60%, 70%, 80%, 90%, 95%, 96%, 97%, 98%, 99%, or 99.9% ee). In some embodiments, the beta blocker is selected from the group consisting of acebutolol, atenolol, betaxolol, bisoprolol, carteolol, celeprolol, labetalol, metoprolol, nadolol, nebivolol, oxprenolol, penbutolol, pindolol, propanolol, sotalol, esmolol, carvedilol, timolol, bopindolol, medroxalol, bucindolol, levobunolol, metipranolol, celiprolol and propafenone. In some embodiments, the beta blocker is oxprenolol or a pharmaceutically acceptable salt thereof. In some embodiments, the composition comprises an enantiomeric excess of at least about 10% (such as at least about any one of 20%, 30%, 40%, 50%, 60%, 70%, 80%, 90%, 95%, 96%, 97%, 98%, 99%, or 99.9%) of S-oxprenolol. In some embodiments, there is provided a method of alleviating one or more symptoms associated with amyotrophic lateral sclerosis, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of alleviating one or more symptoms associated with amyotrophic lateral sclerosis, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg).

In some embodiments, there is provided a method of delaying the development of amyotrophic lateral sclerosis in an individual having amyotrophic lateral sclerosis, comprising administering to the individual an effective amount of an S-enantiomerically enriched composition of a beta blocker or a pharmaceutically acceptable salt thereof (such as a composition having at least about any one of 10%, 20%, 30%, 40%, 50%, 60%, 70%, 80%, 90%, 95%, 96%, 97%, 98%, 99%, or 99.9% ee). In some embodiments, the beta blocker is oxprenolol or a pharmaceutically acceptable salt thereof. In some embodiments, the beta blocker is selected from the group consisting of acebutolol, atenolol, betaxolol, bisoprolol, carteolol, celeprolol, labetalol, metoprolol, nadolol, nebivolol, oxprenolol, penbutolol, pindolol, propanolol, sotalol, esmolol, carvedilol, timolol, bopindolol, medroxalol, bucindolol, levobunolol, metipranolol, celiprolol and propafenone. In some embodiments, the composition comprises oxprenolol or a pharmaceutically acceptable salt thereof. In some embodiments, the composition comprises oxprenolol or a pharmaceutically acceptable salt thereof, wherein the composition is enantiomerically enriched for S-oxprenolol. In some embodiments, the composition comprises an enantiomeric excess of at least about 10% (such as at least about any one of 20%, 30%, 40%, 50%, 60%, 70%, 80%, 90%, 95%, 96%, 97%, 98%, 99%, or 99.9%) of S-oxprenolol. In some embodiments, there is provided a method of delaying the development of amyotrophic lateral sclerosis in an individual having amyotrophic lateral sclerosis, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of delaying the development of amyotrophic lateral sclerosis in an individual having amyotrophic lateral sclerosis, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the method prolongs the survival of the individual by at least any of 1, 2, 3, 4, 5, 6, 7, 8, 9, 10, I I, 12, 18, or 24 months.

In some embodiments, there is provided a method of preventing loss of lean body mass in an individual having amyotrophic lateral sclerosis, comprising administering to the individual an effective amount of an S-enantiomerically enriched composition of a beta blocker or a pharmaceutically acceptable salt thereof (such as a composition having at least about any one of 10%, 20%, 30%, 40%, 50%, 60%, 70%, 80%, 90%, 95%, 96%, 97%, 98%, 99%, or 99.9% ee). In some embodiments, there is provided a method of treating loss oilcan body mass in an individual having amyotrophic lateral sclerosis, comprising administering to the individual an effective amount of an S-enantiomerically enriched composition of a beta blocker or a pharmaceutically acceptable salt thereof (such as a composition having at least about any one of 10%, 20%, 30%, 40%, 50%, 60%, 70%, 80%, 90%, 95%, 96%, 97%, 98%, 99%, or 99.9% ee). In some embodiments, the method of treating loss oilcan body mass is reversing muscle wasting or increasing muscle weight. In some embodiments, the beta blocker is selected from the group consisting of acebutolol, atenolol, betaxolol, bisoprolol, carteolol, celeprolol, labetalol, metoprolol, nadolol, nebivolol, oxprenolol, penbutolol, pindolol, propanolol, sotalol, esmolol, carvedilol, timolol, bopindolol, medroxalol, bucindolol, levobunolol, metipranolol, celiprolol and propafenone. In some embodiments, the beta blocker is oxprenolol or a pharmaceutically acceptable salt thereof. In some embodiments, the composition comprises an enantiomeric excess of at least about 10% (such as at least about any one of 20%, 30%, 40%, 50%, 60%, 70%, 80%, 90%, 95%, 96%, 97%, 98%, 99%, or 99.9%) of S-oxprenolol. In some embodiments, there is provided a method of preventing loss of lean body mass in an individual having amyotrophic lateral sclerosis, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of preventing loss of lean body mass in an individual having amyotrophic lateral sclerosis, comprising administering (such as orally administering) to the individual an effective amount of a composition comprising oxprenolol or a pharmaceutically acceptable salt thereof wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the loss of lean body mass of the individual is no more than about 10% (for example no more than about any of 10%, 9%, 8%, 7%, 6%, or 5%) of the total lean body mass. In some embodiments, the loss of lean body mass is evaluated over a time period of about 1 month to 2 years (for example, about 1, 2, 3, 4, 5, 6, 7, 8, 9, 10, 11, 12, 13, 14, 15, 16, 17, 18, 19, 20, 21, 22, 23, or 24 months).

In some embodiments, there is provided a method of treating muscle wasting in an individual having amyotrophic lateral sclerosis, comprising administering to the individual an effective amount of an S-enantiomerically enriched composition of a beta blocker or a pharmaceutically acceptable salt thereof (such as a composition having at least about any one of 10%, 20%, 30%, 40%, 50%, 60%, 70%, 80%, 90%, 95%, 96%, 97%, 98%, 99%, or 99.9% ee). In some embodiments, the beta blocker is selected from the group consisting of acebutolol, atenolol, betaxolol, bisoprolol, carteolol, celeprolol, labetalol, metoprolol, nadolol, nebivolol, oxprenolol, penbutolol, pindolol, propanolol, sotalol, esmolol, carvedilol, timolol, bopindolol, medroxalol, bucindolol, levobunolol, metipranolol, celiprolol and propafenone. In some embodiments, the beta blocker is oxprenolol or a pharmaceutically acceptable salt thereof. In some embodiments, the composition comprises an enantiomeric excess of at least about 10% (such as at least about any one of 20%, 30%, 40%, 50%, 60%, 70%, 80%, 90%, 95%, 96%, 97%, 98%, 99%, or 99.9%) of S-oxprenolol. In some embodiments, there is provided a method of treating muscle wasting in an individual having amyotrophic lateral sclerosis, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of treating muscle wasting in an individual having amyotrophic lateral sclerosis, comprising administering (such as orally administering) to the individual an effective amount of a composition comprising oxprenolol or a pharmaceutically acceptable salt thereof, wherein the composition is enantiomerically enriched :for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the muscle wasting of the individual is no more than about 10% (for example no more than about any of 10%, 9%, 8%, 7%, 6%, or 5%) of the total body weight. In some embodiments, the muscle wasting is evaluated over a time period of about 1 month to 2 years (for example, about 1, 2, 3, 4, 5, 6, 7, 8, 9, 10, 11, 12, 13, 14, 15, 1.6, 17, 18, 19, 20, 21, 22, 23, or 24 months). In some embodiments, the method leads to a reduction of muscle wasting, i.e., a slow-down of muscle loss in the individual. In some embodiments, the method leads to a reversal of muscle wasting, i.e., an increase in muscle weight in the individual.

In some embodiments, there is provided a method of improving quality of life of an individual having amyotrophic lateral sclerosis, comprising administering to the individual an effective amount of an S-enantiomerically enriched composition of a beta blocker or a pharmaceutically acceptable salt thereof (such as a composition having at least about any one of 10%, 20%, 30%, 40%, 50%, 60%, 70%, 80%, 90%, 95%, 96%, 97%, 98%, 99%, or 99.9% ee). In some embodiments, the beta blocker is selected from the group consisting of acebutolol, atenolol, betaxolol, bisoprolol, carteolol, celeprolol, labetalol, metoprolol, nadolol, nebivolol, oxprenolol, penbutolol, pindolol, propanolol, sotalol, esmolol, carvedilol, timolol, bopindolol, medroxalol, bucindolol, levobunolol, metipranolol, celiprolol and propafenone. In some embodiments, the beta blocker is oxprenolol or a pharmaceutically acceptable salt thereof. In some embodiments, the composition comprises an enantiomeric excess of at least about 10% (such as at least about any one of 20%, 30%, 40%, 50%, 60%, 70%, 80%, 90%, 95%, 96%, 97%, 98%, 99%, or 99.9%) of S-oxprenolol. In some embodiments, there is provided a method of improving quality of life of an individual having amyotrophic lateral sclerosis, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of improving quality of life of an individual having amyotrophic lateral sclerosis, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). Improvement of quality of life can be assessed, for example, by food intake, locomotive activity, improvement in fatigue or dyspnea or global patient assessment scores, in short physical performance battery scores, in standard clinical assessment of functional performance, muscle strength, gait speed, leg strength and hand grip strength, 6-minute corridor walk test, stair climbing power, ability to tolerate courses of chemotherapy and other tests or instruments or questionnaires assessing patient quality of life.

In some embodiments, there is provided a method of increasing food intake of an individual having amyotrophic lateral sclerosis, comprising administering to the individual an effective amount of an S-enantiomerically enriched composition of a beta blocker or a pharmaceutically acceptable salt thereof (such as a composition having at least about any one of 10%, 20%, 30%, 40%, 50%, 60%, 70%, 80%, 90%, 95%, 96%, 97%, 98%, 99%, or 99.9% ee). In some embodiments, the beta blocker is selected from the group consisting of acebutolol, atenolol, betaxolol, bisoprolol, carteolol, celeprolol, labetalol, metoprolol, nadolol, nehivolol, oxprenolol, penbutolol, pindolol, propanolol, sotalol, esmolol, carvedilol, timolol, bopindolol, medroxalol, bucindolol, levobunolol, metipranolol, celiprolol and propafenone. In some embodiments, the beta blocker is oxprenolol or a pharmaceutically acceptable salt thereof. In some embodiments, the composition comprises an enantiomeric excess of at least about 10% (such as at least about any one of 20%, 30%, 40%, 50%, 60%, 70%, 80%, 90%, 95%, 96%, 97%, 98%, 99%, or 99.9%) of S-oxprenolol. In some embodiments, there is provided a method of increasing food intake of an individual having amyotrophic lateral sclerosis, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of increasing food intake of an individual having amyotrophic lateral sclerosis, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg).

In some embodiments, there is provided a method of increasing locomotive activity of an individual having amyotrophic lateral sclerosis, comprising administering to the individual an effective amount of an S-enantiomerically enriched composition of a beta blocker or a pharmaceutically acceptable salt thereof (such as a composition having at least about any one of 10%, 20%, 30%, 40%, 50%, 60%, 70%, 80%, 90%, 95%, 96%, 97%, 98%, 99%, or 99.9% ee).

In some embodiments, the beta blocker is selected from the group consisting of acebutolol, atenolol, betaxolol, bisoprolol, carteolol, celeprolol, labetalol, metoprolol, nadolol, nebivolol, oxprenolol, penbutolol, pindolol, propanolol, sotalol, esmolol, carvedilol, timolol, bopindolol, medroxalol, bucindolol, levobunolol, metipranolol, celiprolol and propafenone. In some embodiments, the beta blocker is oxprenolol or a pharmaceutically acceptable salt thereof. In some embodiments, the composition comprises an enantiomeric excess of at least about 10% (such as at least about any one of 20%, 30%, 40%, 50%, 60%, 70%, 80%, 90%, 95%, 96%, 97%, 98%, 99%, or 99.9%) of S-oxprenolol. In some embodiments, there is provided a method of increasing locomotive activity of an individual having amyotrophic lateral sclerosis, comprising administering to the individual an effective amount of a composition comprising oxprenolol or a pharmaceutically acceptable salt thereof wherein the composition comprises an enantiomeric excess of at least about 99% (for example at least about 99.9%) of S-oxprenolol. In some embodiments, there is provided a method of increasing locomotive activity of an individual having amyotrophic lateral sclerosis, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 ma to about 160 mg (such as about 80 to about 160 mg, for example about 100 mg to about 160 mg).

100761 In some embodiments, there is provided a method of improving fatigue or dyspnea in an individual having amyotrophic lateral sclerosis, comprising administering to the individual an effective amount: of an S-enantiomerically enriched composition of a beta blocker or a pharmaceutically acceptable salt thereof (such as a composition having at least about any one of 10%, 20%, 30%, 40%, 50%, 60%, 70%, 80%, 90%, 95%, 96%, 97%, 98%, 99%, or 99.9% ee). In some embodiments, the beta blocker is selected from the group consisting of acebutolol, atenolol, betaxolol, bisoprolol, carteolol, celeprolol, labetalol, metoprolol, nadolol, nebivolol, oxprenolol, pertbutolol, pindolol, propanolol, sotalol, esmolol, carvedilol, timolol, bopindolol, medroxalol, bucindolol, levobunolol, metipranolol, celiprolol and propafenone. In some embodiments, the beta blocker is oxprenolol or a pharmaceutically acceptable salt thereof. In some embodiments, the composition comprises an enantiomeric excess of at least about 10% (such as at least about any one of 20%, 30%, 40%, 50%, 60%, 70%, 80%, 90%, 95%, 96%, 97%, 98%, 99%, or 99.9%) of S-oxprenolol. In some embodiments, there is provided a method of improving fatigue or dyspnea in an individual having amyotrophic lateral sclerosis, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of improving fatigue or dyspnea in an individual having amyotrophic lateral sclerosis, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg).

In some embodiments, there is provided a method of preventing body weight loss of an individual having amyotrophic lateral sclerosis, comprising administering to the individual an effective amount of an S-enantiomerically enriched composition of a beta blocker or a pharmaceutically acceptable salt thereof (such as a composition having at least about any one of 10%, 20%, 30%, 40%, 50%, 60%, 70%, 80%, 90%, 95%, 96%, 97%, 98%, 99%, or 99.9% ee). In some embodiments, the beta blocker is selected from the group consisting of acebutolol, atenolol, betaxolol, bisoprolol, carteolol, celeprolol, labetalol, metoprolol, nadolol, nebivolol, oxprenolol, penbutolol, pindolol, propanolol, sotalol, esmolol, carvedilol, timolol, bopindolol, medroxalol, bucindolol, levobunolol, metipranolol, celiprolol and propafenone. In some embodiments, the beta blocker is oxprenolol or a pharmaceutically acceptable salt thereof. In some embodiments, the composition comprises an enantiomeric excess of at least about 10% (such as at least about any one of 20%, 30%, 40%, 50%, 60%, 70%, 80%, 90%, 95%, 96%, 97%, 98%, 99%, or 99.9%) of S-oxprenolol. In some embodiments, there is provided a method of preventing body weight loss in an individual having amyotrophic lateral sclerosis, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of preventing body weight loss of an individual having amyotrophic lateral sclerosis, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the body weight loss of the individual is no more than about 20% (for example no more than about any of 15%, 14%, 13%, 12%, 11%, 10%, 9%, 8%, 7%, 6%, or 5%) of the total body weight. In some embodiments, the body weight loss is evaluated over a time period of about 1 month to 2 years (for example, about 1 2, 3, 4, 5, 6, 7, 8, 9, 1.0, 11 12, 13, 14, 15, 16, 17, 18, 19, 20, 21, 22, 23, or 24 months).

In some embodiments, there is provided a method of preventing loss of body fat in an individual having amyotrophic lateral sclerosis, comprising administering to the individual an effective amount of an S-enantiomerically enriched composition of a beta Mocker or a pharmaceutically acceptable salt thereof (such as a composition having at least about any one of 10%, 20%, 30%, 40%, 50%, 60%, 70%, 80%, 90%, 95%, 96%, 97%, 98%, 99%, or 99.9% ee). In some embodiments, the beta blocker is selected from the group consisting of acebutolol, atenolol, betaxolol, bisoprolol, carteolol, celeprolol, labetalol, metoprolol, nadolol, nebivolol, oxprenolol, penbutolol, pindolol, propanolol, sotalol, esmolol, carvedilol, timolol, bopindolol, medroxalol, bucindolol, levobunolol, metipranolol, celiprolol and propafenone. In some embodiments, the beta blocker is oxprenolol or a pharmaceutically acceptable salt thereof. In some embodiments, the composition comprises an enantiomeric excess of at least about 10% (such as at least about any one of 20%, 30%, 40%, 50%, 60%, 70%, 80%, 90%, 95%, 96%, 97%, 98%, 99%, or 99.9%) of S-oxprenolol. In some embodiments, there is provided a method of preventing loss of body fat in an individual having amyotrophic lateral sclerosis, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of preventing loss of body fat in an individual having amyotrophic lateral sclerosis, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, the loss of body fat of the individual is no more than about 10% (for example no more than about any of 15%, 14%, 13%, 12%, 11%, 10%, 9%, 8%, 7%, 6%, or 5%) of the total body fat. In some embodiments, the loss of body fat is evaluated over a time period of about 1 month to 2 years (for example, about 1, 2, 3, 4, 5, 6, 7, 8, 9, 10, 11, 12, 13, 14, 15, 16, 17, 18, 19, 20, 21, 22, 23, or 24 months).

In some embodiments, there is provided a method of providing cardioprotective effects in an individual having amyotrophic lateral sclerosis, comprising administering to the individual an effective amount of an S-enantiomerically enriched composition of a beta blocker or a pharmaceutically acceptable salt thereof (such as a composition having at least about any one of 10%, 20%, 30%, 40%, 50%, 60%, 70%, 80%, 90%, 95%, 96%, 97%, 98%, 99%, or 99.9% ee). In some embodiments, there is provided a method of preventing wasting of a heart muscle in an individual having amyotrophic lateral sclerosis, comprising administering to the individual an effective amount of an S-enantiomerically enriched composition of a beta blocker or a pharmaceutically acceptable salt thereof (such as a composition having at least about any one of 10%, 20%, 30%, 40%, 50%, 60%, 70%, 80%, 90%, 95%, 96%, 97%, 98%, 99%, or 99.9% ee). In some embodiments, the beta blocker is selected from the group consisting of acebutolol, atenolol, betaxolol, bisoprolol, carteolol, celeprolol, labetalol, metoprolol, nadolol, nebivolol, oxprenolol, penbutolol, pindolol, propanolol, sotalol, esmolol, carvedilol, timolol, bopindolol, medroxalol, bucindolol, levobunolol, metipranolol, celiprolol and propafenone. In some embodiments, the beta blocker is oxprenolol or a pharmaceutically acceptable salt thereof. In some embodiments, the composition comprises an enantiomeric excess of at least about 10% (such as at least about any one of 20%, 30%, 40%, 50%, 60%, 70%, 80%, 90%, 95%, 96%, 97%, 98%, 99%, or 99.9%) of S-oxprenolol. In some embodiments, there is provided a method of providing cardioprotective effects in an individual having amyotrophic lateral sclerosis, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of preventing wasting of a heart muscle in an individual having amyotrophic lateral sclerosis, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of providing cardioprotective effects in an individual having amyotrophic lateral sclerosis, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). In some embodiments, there is provided a method of preventing wasting of a heart muscle in an individual having amyotrophic lateral sclerosis, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg). Cardioprotective effects include one or more of the following: preventing and treating atrial fibrillation and ventricular fibrillation, improving arrhythmias, improving diastolic function of a heart, and preventing and treating fibrosis of a heart. The methods described herein are therefore useful for any one or more of these cardioprotective effects.

In some embodiments, there is provided a method of preventing sudden death and/or cardiovascular death in an individual having amyotrophic lateral sclerosis, comprising administering to the individual an effective amount of an S-enantiomerically enriched composition of a beta blocker or a pharmaceutically acceptable salt thereof (such as a composition having at least about any one of 10%, 20%, 30%, 40%, 50%, 60%, 70%, 80%, 90%, 95%, 96%, 97%, 98%, 99%, or 99.9% ee). In some embodiments, the beta blocker is selected from the group consisting of acebutolol, atenolol, betaxolol, bisoprolol, carteolol, celeprolol, labetalol, metoprolol, nadolol, nebivolol, oxprenolol, penbutolol, pindolol, propanolol, sotalol, esmolol, carvedilol, timolol, bopindolol, medroxalol, bucindolol, levobunolol, metipranolol, celiprolol and propafenone. In some embodiments, the beta blocker is oxprenolol or a pharmaceutically acceptable salt thereof. In some embodiments, the composition comprises an enantiomeric excess of at least about 10% (such as at least about any one of 20%, 30%, 40%, 50%, 60%, 70%, 80%, 90%, 95%, 96%, 97%, 98%, 99° A, or 99.9%) of S-oxprenolol. In some embodiments, there is provided a method of preventing sudden death and/or cardiovascular death in an individual having amyotrophic lateral sclerosis, comprising administering to the individual an effective amount of a composition comprising oxprenolol or a pharmaceutically acceptable salt thereof, wherein the composition comprises an enantiomeric excess of at least about 99% (for example at least about 99.9%) of S-oxprenolol. In some embodiments, there is provided a method of preventing sudden death and/or cardiovascular death in an individual having amyotrophic lateral sclerosis, comprising administering (such as orally administering) to the individual an effective amount of a composition comprising oxprenolol or a pharmaceutically acceptable salt thereof, wherein the composition is enantiomerically enriched for S-oxprenolol (for example comprises an enantiomeric excess of at least about 99% of S-oxprenolol), wherein the amount of S-oxprenolol in the composition is about 50 mg to about 160 mg (such as about 80 to about 160 mg, for example about 100 mg to about 160 mg).

The methods described herein may also be useful for any one or more of the following: 1) preventing loss of skeletal muscle associated with amyotrophic lateral sclerosis; 2) treating muscle weakness associated with amyotrophic lateral sclerosis; 3) strengthening skeletal muscle in an individual having amyotrophic lateral sclerosis; 4) treatment of muscle wasting associated with amyotrophic lateral sclerosis; 5) treating dyspnea associated with muscle changes in amyotrophic lateral sclerosis; and 6) improving fatigue resistance of muscle in amyotrophic lateral sclerosis. Skeletal muscle includes, but is not limited to, gastrocnemius muscle, tibialis muscle, soleus muscle, and extensor digitorum longus (EDL) muscle, quadriceps, hamstrings, postural muscles, hand muscles, triceps, biceps, masseter and other jaw muscles, and intercostal and other respiratory muscles. The present application encompasses any of these methods.

In some embodiments, the individual has been diagnosed with or is suspected of having amyotrophic lateral sclerosis. In some embodiments, the individual exhibits one or more symptoms associated with amyotrophic lateral sclerosis. In some embodiments, the individual is a human. In some embodiments, the individual is at least about any of 35, 40, 45, 50, 55, 60, 65, 70, 75, 80, or 85 years old. In some embodiments, the individual is a male. In some embodiments, the individual is a female. In some embodiments, the individual has been previously treated for amyotrophic lateral sclerosis. In some embodiments, the individual has not previously been treated for amyotrophic lateral sclerosis.

Amyotrophic lateral sclerosis covers a spectrum of neurodegenerative syndromes characterized by progressive muscular paralysis reflecting degeneration of motor neurons in the brain and spinal cord. It is a debilitating disease with varied etiology characterized by rapidly progressive weakness, muscle atrophy and fasciculations, muscle spasticity, difficulty speaking (dysarthria), difficulty swallowing (dysphagia), and difficulty breathing (dyspnea).

Amyotrophic lateral sclerosis can be diagnosed by observation of symptoms and signs. An individual may receive neurologic examinations at regular intervals to see whether symptoms are getting worse. Symptoms may include muscle weakness, muscle atrophy. hyperreflexia (overactive reflexes, including twitching and spastic movement), and spasticity (tightening and contraction of muscles, muscle stiffening). Tests can be run to obtain definitive information to diagnose ALS or rule out diseases other than ALS. Such tests include electromyography (EMG), nerve conduction velocity (NCV) test, magnetic resonance imaging (MRI), spinal tap, x-rays, myelogram of the cervical spine, and muscle and/or nerve biopsy.

In some embodiments, the individual has early stage amyotrophic lateral sclerosis. In some embodiments, the individual has middle stage amyotrophic lateral sclerosis. In some embodiments, the individual has late stage amyotrophic lateral sclerosis.

In early stage ALS, the individual can have any of the following symptoms.

| Muscles | Physical effects |
| --- | --- |
| Symptoms may be limited to a single region of the body. Mild symptoms may affect more than one region. Muscles characterized by: Weak and soft or stiff, tight and spastic Cramping and twitching Atrophy (loss of muscle mass) | May experience symptoms such as: Fatigue Poor balance Slurred words Weak grip Tripping when walking |

In middle stage ALS, the individual can have any of the following symptoms.

| Muscles | Physical effects |
| --- | --- |
| Symptoms become more widespread. Some muscles are paralyzed, while others are weakened or unaffected. Twitching may continue. | Unused muscles may cause contractures - joints become rigid, painful and may be deformed. As a result of weak muscles, an individual with ALS may: Require help to stand Have difficulty eating and swallowing, causing choking Have difficulty breathing, especially lying down Some people with ALS experience bouts of uncontrolled and in appropriate laughing or crying (called pseudobulbar affect or PBA). |

In late stage ALS, the individual can have any of the following symptoms.

| Muscles. | Physical effects |
| --- | --- |
| Most voluntary muscles are paralyzed. The ability to move air in and out of the lungs is severely compromised. | Most people in the late stages of ALS have severely limited mobility and are unable to care for their own needs. Fatigue Fuzzy thinking Headaches Susceptibility to pneumonia Speech may no longer be possible Eating and drinking by mouth may no longer be possible |

As used herein, "amyotrophic lateral sclerosis" or "ALS" includes the spectrum of neurodegenerative syndromes known under the names of Classical (Charcot's) ALS, Lou Gehrig's disease, motor neuron disease (MND), progressive bulbar palsy (PRP), progressive muscular atrophy (PMA), primary lateral sclerosis (PLS), bulbar onset ALS, spinal onset ALS and ALS with multi-system involvement (Wijesekera L C and Leigh P N. Amyotrophic lateral sclerosis. Orphanet Journal of Rare Disease 2009, 4:3). Types of ALS include sporadic ALS, familial ALS, Western Pacific ALS, Juvenile ALS, and Hirayama Disease.

Types of ALS include sporadic ALS, familial ALS, and variants, including Western Pacific ALS, Juvenile ALS, and Hirayama Disease. The present disclosure provides a method for treating ALS, including sporadic ALS, familial ALS, and variants, including Western Pacific ALS, Juvenile ALS, and Hirayama Disease.

Approximately 10% of cases of ALS are familial. The remaining 90% are sporadic and though to be multifactorial, with both environmental and genetic components contributing to disease susceptibility. The genetics of both FALS and SALS is complex. About 20% of cases with autosomal dominant FALS and 2% of patients with SALS show mutations in the copper/zinc superoxide dismutase (SOD1) gene on chromosome 21. Mutations in the gene are thought to cause disease through a toxic gain of function rather than causing impairment of the antioxidant function of the SOD 1 enzyme. Although genes different from other than SOD1 have been associated with familial ALS, including alsin (ALS2), senataxin (ALS4) or Angiogenin, the genetic defect remains to be identified in the majority of cases.

Sporadic and familial ALS (SALS and FALS, respectively) are clinically and pathologically similar, suggesting a common pathogenesis. Both forms produce similar pathological hallmarks, including progressive muscle weakness, atrophy, and spasticity, each of which reflects the degeneration and death of upper and lower motor neurons. Denervation of the respiratory muscles and diaphragm is generally the fatal event. In current medical practice, the terms "bulbar onset ALS" and "spinal onset ALS" have replaced the terms PBP and Charchot's ALS. Approximately two thirds of patients with typical ALS have a spinal form of the disease (limb onset) and present symptoms related to focal muscle weakness and wasting, where the symptoms may start either distally or proximally in the upper and lower limbs. Gradually, spasticity may develop in the weakened atrophic limbs, affecting manual dexterity and gait. Patients with bulbar onset ALS usually present with dysarthria and dysphagia for solid or liquids, and limbs symptoms can develop almost simultaneously with bulbar symptoms, and in the vast majority of cases will occur within 1-2 years. Paralysis is progressive and leads to death due to respiratory failure within 2-3 years for bulbar onset cases and 3-5 years for limb onset ALS cases.

Western Pacific ALS is a unique neurological disease initially identified among the Chamorro people of Guam and is characterized by a combination of symptoms including stooped posture, a blank expressionless face, dementia, slow shuffling movement, a resting tremor that stops upon deliberate action, slow movements, and muscle atrophy that results in muscles dipping down in the hand. Some patients have Parkinsonism features combined with dementia (Parkinsonism Dementia Complex, PDC). In still others, only dementia is observed. Neuropathologically, all clinical forms of the disease result in a specific feature, neurofibrillary tangles, found in the cortex and in the spinal cord. Because the disease has aspects that resemble amyotrophic lateral sclerosis (ALS), Parkinson's disease (PD) and Alzheimer's disease (AD), this disease is known as Western Pacific ALS or amyotrophic lateral sclerosis-Parkinsonism dementia complex of Guam (ALS-PDC) and is also known as lytico-bodig.

Juvenile ALS is an adolescent motor neuron disease that is clinically indistinguishable from ALS. Onset is between ages of twelve and sixteen years and occurs below the age of 25 years.

In Hirayama Disease, there is localized atrophy of one arm associated with increased reflexes implicating the presence of upper and lower motor neuron damage. However, Hirayama Disease involves a problem at the junction between the cervical spine and the skull where there is pressure on the cervical spinal cord. In order to detect Hirayama Disease, an MRI of the neck needs to be performed in different positions including neck flexion and extension.

Other syndromes related to the ALS spectrum of disorders include progressive bulbar palsy (PBP), progressive muscular atrophy (PMA), primary lateral sclerosis (PLS) and ALS with multi-system involvement. The present disclosure provides a method for treating a syndrome related to the ALS spectrum of disorders, such as progressive bulbar palsy (PBP), progressive muscular atrophy (PMA), primary lateral sclerosis (PLS), or ALS with multi-system involvement.

Progressive bulbar palsy (PBP) is a motor neuron disease, in which the nerves supplying the bulbar muscles are attacked. PBP is characterized by the degeneration of motor neurons in the cerebral cortex, spinal cord, brain stem, and pyramidal tracts. Progressive bulbar palsy symptoms can include progressive difficulty with chewing, talking, and swallowing. Patients can also exhibit reduced gag reflexes, weak palatal movements, fasciculations, and weak movement of the facial muscles and tongue. In advanced cases of PBP, the patient may be unable to protrude their tongue or manipulate food in their mouth.

Progressive muscular atrophy (PMA, also Duchenne-Aran muscular atrophy or Duchenne-Aran disease) is motor neuron disease which affects the lower motor neurons. Symptoms of PMA include atrophy, fasciculation, and muscle weakness. Some patients have symptoms restricted to the arms or legs.

Primary lateral sclerosis (PLS) is a neuromuscular disease characterized by progressive muscle weakness in the voluntary muscles. PLS affects upper motor neurons. Symptoms include difficulty with balance and weakness and stiffness in the legs. Other common symptoms are spasticity (involuntary muscle contraction due to the stretching of muscle). There may also be difficulty in breathing in the later stages of the disease, causing those patients who develop ventilatory failure. Hyperreflexia is another feature of PLS as seen in patients presenting with the Babinski's sign. Some people present with emotional lability and bladder urgency, and occasionally people with PLS experience mild cognitive changes detectable on neuropsychological testing, particularly on measures of executive function.

In some embodiments, the benefits of administering the compositions to alleviate the symptoms or treat ALS can be evaluated by the following tests: a reduction in the rate of decrease in the ALSFRS-R score, the Manual Muscle Testing (MMT) score, the Slow Vital Capacity (VC) percent predicted value, the ALS-Specific Quality of Life (ALSSQoL) score, and EuroQol-5 Dimensions (EQ-5D) Health Outcomes Scale score. Another suitable test for evaluation includes a reduction in the rate of increase in the Zarit Burden Interview (ZBI) score. Another suitable test for evaluation is the use of electrical impedance myography as a biomarker (Rutkove et al., Amyotroph Lateral Scler. 2012 September; 13(5):439-4). In some embodiments, the rate of decrease in, or the symptom measured by, the ALSTRS-R score is reduced by at least 15% as compared to an individual with ALS who is not administered S-oxprenolol.

Beta Blockers

The methods described herein comprise administration of compositions comprising beta blockers. Beta blockers, which are used to treat hypertension, can be used for preventing the onset of amyotrophic lateral sclerosis and for treating amyotrophic lateral sclerosis. For example, the use of a beta blocker in an individual with ALS has shown that the individual has prolonged survival compared to an individual with ALS that did not receive a beta blocker. Other benefits of the use of a beta blocker include preservation of lean body mass and prevention of body weight loss. These effects suggest that beta blockers can be used to treat ALS, delay the development of ALS, alleviate the symptoms of ALS, and improve the quality of life for ALS patients.

In some embodiments, the beta blocker has intrinsic sympathomimetic activity (ISA). In some embodiments, the beta blocker does not have intrinsic sympathomimetic activity (ISA). Intrinsic sympathomimetic activity is used to refer to beta blockers that can show both agonism and antagonism at a given beta receptor, depending on the concentration of the agent (beta blocker) and the concentration of the antagonized agent.

In some embodiments, where the beta blocker contains one chiral center, the beta blocker is the enantiomerically enriched S-enantiomer or a pharmaceutically acceptable salt thereof.

In some embodiments, the beta blocker is selected from the group consisting ofacebutolol, atenolol, betaxolol, bisoprolol, carteolol, celeprolol, labetalol, metoprolol, nadolol, nebivolol, oxprenolol, penbutolol, pindolol, propanolol, sotalol, esmolol, carvedilol, timolol, bopindolol, medroxalol, bucindolol, levobunolol, metipranolol celiprolol and propafenone. In some embodiments, the beta blocker is oxprenolol. Oxprenolol is a non-selective beta blocker which possesses some intrinsic sympathomimetic activity.

In some embodiments, the beta blocker also has partial 5-HT$_{1A}$ agonism activity. The 5-HT$_{1A}$ receptor is a subtype of 5-HT receptor that binds the endogenous neurotransmitter serotonin (5-hydroxytryptamine, 5-HT). Oxprenolol is a partial 5-HT1a agonist.

S-Enantiomerically Enriched Compositions of Beta Blockers

The methods described herein comprise administration of an S-enantiomerically enriched composition of a beta blocker or a pharmaceutically acceptable salt thereof (for example comprising an enantiomeric excess of at least about 99% of a beta blocker). The present disclosure also provides such compositions which are useful for the methods disclosed herein.

When a compound has a chiral center, the compound can exist in optically active forms. Optically active compounds have the ability to rotate the plane of plane-polarized light. In describing an optically active compound, the prefixes R and S are used to denote the absolute configuration of the molecule about its chiral center(s). The prefixes "d" and "l" or (+) and (−) are employed to designate the sign of rotation of plane-polarized light by the compound, with (−) or l meaning that the compound is "levorotatory" and with (+) or d meaning that the compound is "dextrorotatory." There is no correlation between nomenclature for the absolute stereochemistry and for the rotation of an enantiomer. For a given chemical structure, these compounds, called "stereoisomers," are identical except that they are mirror images of one another. A specific stereoisomer can also be referred to as an "enantiomer," and a mixture of such isomers is often called an "enantiomeric" or "racemic" mixture. When a compound has one chiral center, there are two enantiomers: the S-enantiomer and the R-enantiomer.

The compositions described herein are enantiomerically enriched for S-enantiomer. For example, in some embodiments, the composition comprises an enantiomeric excess of at least about 1%, 5%, 10%, 15%, 20%, 25%, 30%, 35%, 40%, 45%, 50%, 55%, 60%, 65%, 70%, 75%, 80%, 85%, 90% or 95% of S-enantiomer of the beta blocker. In some embodiments, the composition comprises an enantiomeric excess of at least about 90%, 91%, 92%, 93%, 94%, 95%, 96%, 97%, 98%, 99%, or 99.9% of S-enantiomer of the beta blocker. In some embodiments, the composition comprises an enantiomeric excess of at least about 90%, 95%, 98%, 99%, or 100%, up to the detectable limit of purity, of S-enantiomer of the beta blocker. In some embodiments, the composition comprises an enantiomeric excess of any of about 1-4%, 5-9%, 10-11%, 20-29%, 30-39%, 40-49%, 50-59%, 60-69%, 70-79%, 80- 89%, 90-99, or 100% of S-enantiomer of the beta blocker. In some embodiments, the composition comprises an enantiomeric excess of at least about 99% or 100% of S-enantiomer of the beta blocker (i.e., pure S-enantiomer of the beta blocker). In some embodiments, the composition comprises an enantiomeric excess of at least 99.1, 99.2, 99.3, 99.4, 99.5, 99.6, 99.7, 99.8, 99.9 or 100% of S-enantiomer of the beta blocker (i.e., pure S-enantiomer of the beta blocker). Methods of making enantiomerically enriched compositions of beta blockers are known in the art.

In some embodiments, the beta blocker is selected from the group consisting of acebutolol, atenolol, betaxolol, bisoprolol, carteolol, celeprolol, labetalol, metoprolol, nadolol, nebivolol, oxprenolol, penbutolol, pindolol, propanolol, sotalol, esmolol, carvedilol, timolol, bopindolol, medroxalol, bucindolol, levobunolol, metipranolol, celiprolol and propafenone or a pharmaceutically acceptable salt thereof.

In some embodiments, the beta blocker is oxprenolol or a pharmaceutically acceptable salt thereof. Oxprenolol is 1-[2-(allyloxy)phenoxy]-3-(isopropylatnino)propan-2-ol. The structure of oxprenolol is shown below.

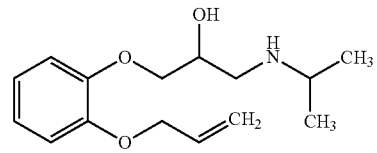 [SMILES: C=CCOc1ccccc1OCC(O)CNC(C)C]

Oxprenolol is a compound with one chiral center. As a racemic mixture, there is a mixture of (R)-(+-oxprenolol and (S)-(−)oxprenolol. Analytical methods, such as HPLC, can be used for separation and quantification of (R)-(+)-oxprenolol and (S)-(−)-oxprenolol in mixtures. The structures of (R)-(+)-oxprenolol and (S)-(−)-oxprenolol are shown below.

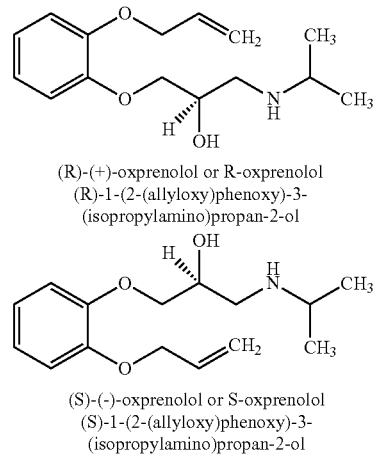

(R)-(+)-oxprenolol or R-oxprenolol
(R)-1-(2-(allyloxy)phenoxy)-3-
(isopropylamino)propan-2-ol (S)-(-)-oxprenolol or S-oxprenolol
(S)-1-(2-(allyloxy)phenoxy)-3-
(isopropylamino)propan-2-ol The compositions described herein are enantiomerically enriched for S-oxprenolol. For example, in some embodiments, the composition comprises an enantiomeric excess of at least about 1%, 5%, 10%, 15%, 20%, 25%, 30%, 35%, 40%, 45%, 50%, 55%, 60%, 65%, 70%, 75%, 80%, 85%, 90% or 95% of S-oxprenolol. In some embodiments, the composition comprises an enantiomeric excess of at least about 90%, 91%, 92%, 93%, 94%, 95%, 96%, 97%, 98%, 99%, or 99.9% of S-oxprenolol. In some embodiments, the composition comprises an enantiomeric excess of at least about 90%, 95%, 98%, 99%, or 100%, up to the detectable limit of purity, of S-oxprenolol. In some embodiments, the composition comprises an enantiomeric excess of any of about 1-4%, 5-9%, 10-11%, 20-29%, 30-39%, 40-49%, 50-59%, 60-69%, 70-79%, 80-89%, 90-99, or 100% of S-oxprenolol. In some embodiments, the composition comprises an enantiomeric excess of at least about 99% or 100% of S-oxprenolol (i.e., pure S-oxprenolol). In some embodiments, the composition comprises an enantiomeric excess of at least 99.1, 99.2, 99.3, 99.4, 99.5, 99.6, 99.7, 99.8, 99.9 or 100% of S-oxprenolol (i.e., pure S-oxprenolol). Methods of making enantiomerically enriched compositions of oxprenolol are known in the art.

Two main routes are established for obtaining enantiomerically enriched compounds: (1) asymmetric syntheses and (2) racemic resolutions. (R. A. Sheldon: *The Industrial Synthesis of Optically Active Compounds*, in Miklós Simonyi (editor), *Problems and Wonders if Chiral Molecules*, Akadémiai. Kiadó, Budapest, 1990, S. 349-386). The syntheses give medium-high yields and excellent enantiomeric excess, but the resolutions are limited by 50% yield. Both technologies involve techniques such as dynamic kinetic resolution (DKR) and membrane-based extraction (Augustian J et al., Process Biochemistry Volume 45, Issue 10, October 2010, Pages 1587-4604). One method describes enantiomer enrichment of oxprenolol up to 68% enantiomeric excess was achieved by using a cellulose tris(3,5-dimethylphenylcarbamate) (CTPC)-coated rayon-belt. (Yashima E. et al., Tetrahedron: Asymmetry Volume 6, Issue 8, August 1995, Pages 1889-1890).

The compositions described herein in some embodiments are present in pharmaceutical compositions. The pharmaceutical compositions may further comprise one or more pharmaceutically acceptable carrier (or excipients). A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In some embodiments, the pharmaceutical composition is sterile.

Also provided here are unit dosage forms comprising a pharmaceutical compositions described herein. These unit dosage forms can be stored in a suitable packaging in single or multiple unit dosages and may also be further sterilized and sealed. Unit dosage forms can be provided, for example, in the form of tablets, capsules, vials, and any other forms described herein.

In some embodiments, there is provided a composition (such as a pharmaceutical composition, for example a unit dosage) comprising oxprenolol or a pharmaceutically acceptable salt thereof, wherein the composition is enantiomerically enriched for S-oxprenolol (for example comprising an enantiomeric excess of at least about 99% of S-oxprenolol), wherein the amount of S-oxprenolol in the composition (such as pharmaceutical composition) is included in any of the following ranges: about 5 to about 10 mg, about 10 to about 20 mg, about 20 to about 30 mg, about 30 to about 40 mg, about 40 to about 50 mg, about 50 to about 60 mg, about 60 to about 70 mg, about 70 to about 80 mg, about 80 to about 90 mg, about 90 to about 100 mg, about 100 to about 110 mg, about 110 to about 120 mg, about 120 to about 130 mg, about 130 to about 140 mg, about 140 to about 150 mg, about 150 to about 160 mg. In some embodiments, the amount of S-oxprenolol in the composition is about 20 to about 160 mg, including for example about 50 to about 150 mg, 80 to about 150 ma, about 90 to about 140 mg, about 100 to about 120 mg. In some embodiments, the composition is suitable for oral administration.

In some embodiments, the composition is provided in a slow release form. For example, oxprenolol can be administered in slow release form. (Eur J Drug Metab Pharmacokinet. 1998 April-June; 23(2):178-84; Bennett P N, Bennett J, Bradbrook I, Francis J, John V A, Rogers H, Turner P, Warrington S J. Br J Clin Pharmacol. 1985; 19 Supp 2:171S-175S; and Woods K L, Jack D B, Kendall M J, Halsey A, O'Donnell M L, Warrington S J, John V A. Br J Clin Pharmacol. 1985; 19 Suppl 2:177S-184S.)

Also provided are articles of manufacture comprising the compositions, formulations, and unit dosages described herein in suitable packaging for use in the methods of treatment, methods of administration, and dosage regimens described herein. Suitable packaging for compositions described herein are known in the art, and include, for example, vial (such as sealed vials), vessels (such as sealed vessels), ampules, bottles, jars, flexible packaging (e.g., sealed Mylar or plastic bags), and the like. These articles of manufacture may further be sterilized and/or sealed.

Dosages and Administration Route

The dosage of the compositions described herein administered to an individual (such as a human) may vary with the particular composition, the method of administration, and the particular stage of amyotrophic lateral sclerosis. The amount should be sufficient to produce a desirable response, such as a therapeutic or prophylactic response against amyotrophic lateral sclerosis. In some embodiments, the amount of the composition is a therapeutically effective amount. In some embodiments, that amount of the composition is a prophylactically effective amount. In some embodiments, the amount of total oxprenolol in the composition is below the level that induces a toxicological effect (i.e., an effect above a clinically acceptable level of toxicity) or is at a level where a potential side effect can he controlled or tolerated when the composition is administered to the individual.

In some embodiments, the amount of an S-enantiomerically enriched composition of a beta blocker or a pharmaceutically acceptable salt thereof (e.g., S-oxprenolol) in the composition is included in any of the following ranges: about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg. In some embodiments, the amount of an S-enantiomerically enriched composition of a beta blocker or a pharmaceutically acceptable salt thereof (e.g., S-oxprenolol) in the composition is included in any of the following ranges: about 5 to about 10 mg, about 10 to about 20 mg, about 20 to about 30 mg, about 30 to about 40 mg, about 40 to about 50 mg, about 50 to about 60 mg, about 60 to about 70 mg, about 70 to about 80 mg, about 80 to about 90 mg, about 90 to about 100 mg, about 100 to about 110 mg, about 110 to about 120 mg, about 120 to about 130 mg, about 130 to about 140 mg, about 140 to about 150 mg, about 150 to about 160 mg. In some embodiments, the amount of an S-enantiomerically enriched composition of a beta blocker or a pharmaceutically acceptable salt thereof (e.g., S-oxprenolol) in the composition is about 20 to about 160 mg, including for example about 50 to about 150 mg, 80 to about 150 mg, about 90 to about 140 mg, about 100 to about 120 mg.

In some embodiments, the amount of an S-enantiomerically enriched composition of a beta blocker or a pharmaceutically acceptable salt thereof (e.g., S-oxprenolol) in the composition includes at least about any of 0.1 mg/kg, 0.5 mg/kg, 1 mg/kg, 2.5 mg/kg, 5 mg/kg, 7.5 mg/kg, 10 mg/kg, 15 mg/kg, or 20 mg/kg. In some embodiments, the amount of an S-enantiomerically enriched composition of a beta blocker or a pharmaceutically acceptable salt thereof (e.g., S-oxprenolol) in the composition includes less than about any of 35 mg/kg, 30 mg/kg, 25 mg/kg, 20 mg/kg, 15 mg/kg, 10 mg/kg, 5 mg/kg, 2.5 mg/kg, 2 mg/kg, 1 mg/kg, 0.5 mg/kg, or 0.1 mg/kg.

Exemplary dosing frequencies include, but are not limited to, weekly without break; weekly, three out of four weeks; once every three weeks; once every two weeks; weekly, two out of three weeks. In some embodiments, the composition is administered about once every 2 weeks, once every 3 weeks, once every 4 weeks, once every 6 weeks, or once every 8 weeks. In some embodiments, the composition is administered at least about any of 1×, 2×, 3×, 4×, 5×, 6×, or 7× (i.e., daily) a week. In some embodiments, the intervals between each administration are less than about any of 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week. In some embodiments, the composition is administered daily. In some embodiments, the composition is administered twice daily. In some embodiments, the composition is administered at least once (such as at least any of 2×, 3×, or 4×) daily.

The administration of the composition can be extended over an extended period of time, such as from about a month up to about seven years or life-long. In some embodiments, the composition is administered over a period of at least about any of 2, 3, 4, 5, 6, 7, 8, 9, 10, 11, 12, 18, 24, 30, 36, 48, 60, 72, or 84 months or life-long. In some embodiments, the composition is administered over a period of at least one month, wherein the interval between each administration is no more than about a week.

The compositions described herein can be administered to an individual (such as human) via various routes, including, for example, intravenous, intra-arterial, intraperitoneal, intraportal, intrapulmonary, oral, inhalation, intravesicular, intramuscular, intra-tracheal, subcutaneous, intraocular, intrathecal, transmucosal, and transdermal. In some embodiments, sustained continuous release formulation of the composition may be used.

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

Pharmaceutical Formulations and Administration

The pharmaceutical compositions described herein may be formulated as solutions, emulsions, suspensions, dispersions, or inclusion complexes such as cyclodextrins in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the embodiments may be administered by a suitable route of delivery, such as oral, parenteral, rectal, nasal, topical, or ocular routes, or by inhalation. Preferably, the compositions are formulated for intravenous or oral administration.

For oral administration, the compositions may be provided in a solid form, such as a tablet or capsule, or as a solution, emulsion, or suspension. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating. The oral formulations may be presented as discrete units such as capsules, cachets or tablets, each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

A tablet may be made by compression or moulding, optionally with one or more accessory ingredients. Compressed tablets may be prepared by compressing in a suitable machine the active ingredient in a free-flowing form such as a powder or granules, optionally mixed with a binder (eg povidone, gelatin, hydroxypropylmethyl cellulose), lubricant, inert diluent, preservative, disintegrant (eg sodium starch glycolate, cross-linked povidone, cross-linked sodium carboxymethyl cellulose), surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethylcellulose in varying proportions to provide desired release profile.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

For parenteral use, including intravenous, intramuscular, intraperitoneal, intranasal, or subcutaneous routes, the compositions may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Formulations suitable for parenteral including intravenous administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose or art appropriate fraction thereof, of an active ingredient.

Drug Combinations

The methods of the embodiments comprise administering an effective amount of at least one compound of the embodiments; optionally the compound may be administered in combination with one or more additional therapeutic agents, particularly therapeutic agents known to be useful for treating a amyotrophic lateral sclerosis afflicting the subject.

The additional active ingredients may be administered in a separate pharmaceutical composition from a compound of the embodiments or may be included with a compound of the embodiments in a single pharmaceutical composition. The additional active ingredients may be administered simultaneously with, prior to, or after administration of a compound of the embodiments.

In certain embodiments, the additional therapeutic agent is selected from the group consisting of CK-2017357, olesoxime (TRO 19622), arimoclomol, riluzole, tretionin and pioglitazone HCl, AVP-923, memantine, talampanel, tauroursodeoxycholic acid (TUDCA), thalidomide, olanzapine, KNS-760704, lithium carbonate, NPOO1, ONO-2 506PO, tamoxifen, creatine monohydrate, coenzyme Q10, YAM80, sodium phenylbutyrate, pyrimethamine, R(+) pramipexole dihydrochloride monohydrate, vitamin E, minocycline, topiramate, gabapentin, AEOL-10150, stem cell injections, SB-509, autologous bone marrow-derived stern cells, ceftriaxone, E0302 (mecobalamin), MCI-186, glatiramer acetate, insulin-like growth factor-1 (IGF-1), ISIS 333611, sNN0029, GSK1223249, brain-derived neurotrophic factor (BDNF), and anti-CD40L antibody.

Kits

The present application also provides kits, medicines, compositions, and unit dosage forms for use in any of the methods described herein.

Kits provided herein include one or more containers comprising any one of the compositions described herein and/or other agent(s), and in some embodiments, further comprise instructions for use in accordance with any of the methods described herein. The kit may further comprise a description of selection of individual suitable for treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a) an S-enantiomerically enriched composition of a beta blocker or a pharmaceutically acceptable salt thereof (e.g., S-oxprenolol) and a pharmaceutically acceptable carrier and b) instructions for administering the composition for treatment of amyotrophic lateral sclerosis.

The kits of the invention are in suitable packaging. Suitable packaging include, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the compositions generally include information as to dosage, dosing schedule, and route of administration for the intended treatment. The containers may be unit doses, bulk packages (e.g., multi-dose packages) or sub-unit doses. For example, kits may be provided that contain sufficient dosages of S-oxprenolol as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the pharmaceutical compositions and instructions for use and packaged in quantities sufficient for storage and use in pharmacies, for example, hospital pharmacies and compounding pharmacies.

Also provided are medicines, compositions, and unit dosage forms useful for the methods described herein. For example, the present disclosure provides, in some embodiments, an S-enantiomerically enriched composition of a beta blocker or a pharmaceutically acceptable salt thereof (e.g., S-oxprenolol) for treating amyotrophic lateral sclerosis in an individual having amyotrophic lateral sclerosis. The present disclosure provides, in some embodiments, an S-enantiomerically enriched composition of a beta blocker or a pharmaceutically acceptable salt thereof (e.g., S-oxprenolol) for prolonging survival of an individual having amyotrophic lateral sclerosis. The present disclosure provides, in some embodiments, an S-enantiomerically enriched composition of a beta blocker or a pharmaceutically acceptable salt thereof (e.g., S-oxprenolol) for delaying the development of amyotrophic lateral sclerosis in an individual having amyotrophic lateral sclerosis. The present disclosure provides, in some embodiments, an S-enantiomerically enriched composition of a beta blocker or a pharmaceutically acceptable salt thereof (e.g., S-oxprenolol) for preventing lean mass loss of an individual having amyotrophic lateral sclerosis.

The present disclosure provides, in some embodiments, an S-enantiotnerically enriched composition of a beta blocker or a pharmaceutically acceptable salt thereof (e.g., S-oxprenolol) for preventing muscle wasting of an individual having amyotrophic lateral sclerosis. The present disclosure provides, in some embodiments, an S-enantiomerically enriched composition of a beta blocker or a pharmaceutically acceptable salt thereof (e.g., S-oxprenolol) for improving quality of life in an individual having amyotrophic lateral sclerosis.

For example, the present disclosure provides, in some embodiments, an S-enantiomerically enriched composition of a beta blocker or a pharmaceutically acceptable salt thereof (e.g., S-oxprenolol) for the manufacture of a medicament for treating amyotrophic lateral sclerosis in an individual having amyotrophic lateral sclerosis. The present disclosure provides, in some embodiments, an S-enantiomerically enriched composition of a beta blocker or a pharmaceutically acceptable salt thereof (e.g., S-oxprenolol) for the manufacture of a medicament for prolonging survival of an individual having amyotrophic lateral sclerosis. The present disclosure provides, in some embodiments, an S-enantiomerically enriched composition of a beta blocker or a pharmaceutically acceptable salt thereof (e.g., S-oxprenolol) for the manufacture of a medicament for delaying the development of amyotrophic lateral sclerosis in an individual having amyotrophic lateral sclerosis. The present disclosure provides, in some embodiments, an S-enantiomerically enriched composition of a beta blocker or a pharmaceutically acceptable salt thereof (e.g., S-oxprenolol) for the manufacture of a medicament for preventing lean mass loss of an individual having amyotrophic lateral sclerosis. The present disclosure provides, in some embodiments, an S-enantiomerically enriched composition of a beta blocker or a pharmaceutically acceptable salt thereof (e.g., S-oxprenolol) for the manufacture of a medicament for preventing muscle wasting of an individual having amyotrophic lateral sclerosis. The present disclosure provides, in some embodiments, an S-enantiomerically enriched composition of a beta blocker or a pharmaceutically acceptable salt thereof (e.g., S-oxprenolol) for the manufacture of a medicament for improving quality of life in an individual having amyotrophic lateral sclerosis.

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

EXAMPLES

Example 1

Synthesis S-Oxprenolol

The synthesis of S-oxprenolol is shown in Scheme 1.

Scheme 1

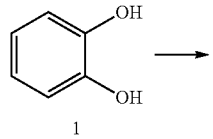

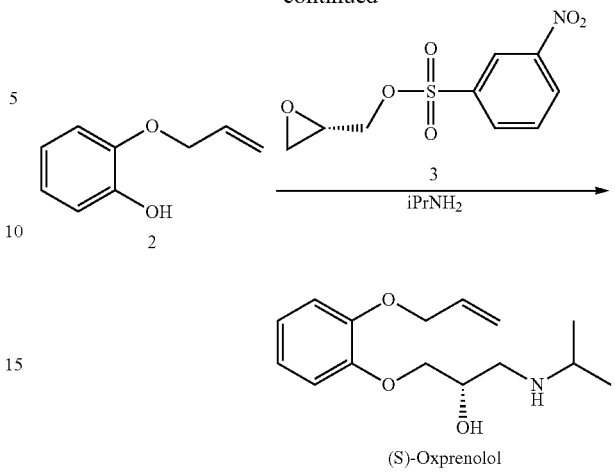

Preparation of 2-(Allyloxy)Phenol

To a solution of catechol (1) (40.0 g, 0.364 mol) in acetone (160 mL) was added potassium carbonate (50.0 g, 0.363 mol) portion-wise at room temperature, over a period of 30 minutes. After the addition was complete the mixture was stirred at room temperature for 1 hour. Allyl bromide (31.0 mL, 0.358 mol) was then added over a period of 30 minutes, and the reaction heated to 60-70° C. for 6 hours. The reaction was allowed to cool, then water and ethyl acetate were added and the mixture was separated. The organic layer was dried (MgSO$_4$) and the solvent evaporated to give 2-(allyloxy)phenol, (2) (46.2 g) as a 7:3 mixture of mono and bis alkylated material.

$^1$H NMR (300 MHz, CDCl$_3$) δ 6.93-6.77 (m, 4H), 6.05 (m, 1H), 5.41 (dd, 1H), 5.30 (m, 1H), 4.61 (d, 2H). LCMS: Rt 0.70 min, [M+H]$^+$ 148.9, 70%.

Preparation of S-Oxprenolol

CsF (22.8 g, 0.150 mol) was added to a solution of 2-(allyloxy)phenol (7.50 g, 0.050 mol) in DMF (100 mL) and stirred for 1 hour at room temperature. (S)-Glycidyl nosylate (13.0 g, 0.050 mol) was added and the reaction stirred for 72 hours at room temperature, then added dropwise to $^i$PrNH$_2$ (97 mL, 1.26 mol) and stirred overnight. The reaction mixture was diluted with EtOAc (150 mL) and water (200 mL) and the solids removed by filtration. The phases were separated and the organic layer washed with water (100 mL), then brine (100 mL), dried over MgSO$_4$ and concentrated. Purification by column chromatography (5-10% MeOH/DCM then 5% (17% NH$_3$/MeOH) in DCM) gave (S)-oxprenolol (4.67 g, 20%) as a brown solid.

$^1$H NMR (300 MHz, CDCl$_3$) δ 6.92-6.89 (m, 2H), 6.82-6.79 (m, 2H), 5.99 (m, 1H), 5.37 (d, 1H), 5.21 (d, 1H), 4.87 (br s, 1H), 4.51 (d, 2H), 3.85 (d, 2H), 3.80 (m, 1H), 2.69-2.61 (m, 2H), 2.47 (m, 1H), 1.48 (br s, 1H), 0.93 (d, 6H).

LCMS: Rt 1.78 min, [M+H]$^+$ 266.1, 100%.

Example 2

Synthesis of R-Oxprenolol

The synthesis of S-oxprenolol is shown in Scheme 2.

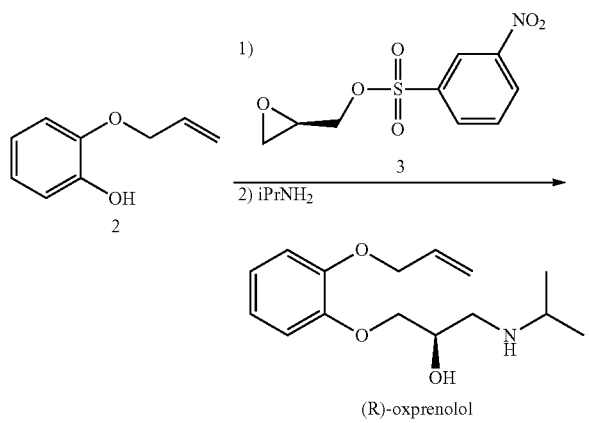

Scheme 2

(R)-oxprenolol

Preparation of R-Oxprenolol

CsF (2.95 g, 19.4 mmol) and $K_2CO_3$ (17.3 g, 125 mmol) were added to a solution of 2-(allyloxy)phenol (14.4 g, 96.2 mmol) in DMF (250 mL) and stirred for 30 minutes at room temperature. (R)-Glycidyl nosylate (25.0 g, 96.4 mmol) was added and the reaction stirred for 48 hours at room temperature. $^iPrNH_2$ (190 mL, 2.21 mol) was added in one portion and the reaction stirred for 72 hours. The reaction mixture was diluted with water (1.0 L) and extracted with EtOAc (3×300 mL). The combined organics were washed with HCl (2.0 M, 3×300 mL). The aqueous layer was pH adjusted to pH 12 with NaOH (2.0 M) and extracted into EtOAc (2×500 mL). This was washed with 1:1 water/brine (3×500 mt.), then with brine (500 mL), dried over $Na_2SO_4$ and concentrated. The crude solid was triturated from heptanes, filtered and dried under vacuum at 40° C. overnight to give (R)-oxprenolol (24.5 g, 69%) as a brown solid.

$^1$H NMR (300 MHz, $CDCl_3$) δ 6.92-6.89 (m, 2H), 6.82-6.79 (m, 2H), 5.99 (m, 1H), 5.37 (d, 1H), 5.21 (d, 1H), 4.87 (br s, 1H), 4.51 (d, 2H), 3.85 (d, 2H), 3.80 (m, 1H), 2.69-2.61 (m, 2H), 2.47 (m, 1H), 1.48 (br s, 1H), 0.93 (d, 6H).

LCMS: Rt 1.79 min, $[M+H]^{30}$ 266.1, 99%.

Example 3

Study Protocol with B6SJL-Tg(SOD1*G93A)1Gur/J ALS Mouse Model

Transgenic mice over-expressing a high copy number (25 copies) of mutated human SOD1 gene with a G93A point mutation, i.e., B6SJL-TgN [SOD1-C93A]1Gur (B1H-G93A transgenic mice, JR2726; Hemizygote) (Gurney M E, et al., Science, 264, 1772-1775, 1994) ("G93A SOD1 B6SJL hybrid (G93A) model"), were used. As shown in a diagram in FIG. 1, the transgenic mice display muscle weakness and atrophy by 90 to 100 days of age, and typically die near 130 days of age.

An intervention study was performed with S-oxprenolol (10 mg/kg/day) in the G93A SOD1 B6SJL hybrid (G93A) model after onset of AILS. Onset of disease was defined as peak body weight as well as the beam walk and splay neurological scores as suggested by Ludolph et al. 2007. (Ludolph A C, Bendotti C, Blaugrund E, Hengerer B, Loftier J P, Martin J, Meininger V, Meyer T, Moussaoui S, Robberecht W, Scott S, Silani V, Van Den Berg L H (ENMC Group For The Establishment Of Guidelines For The Conduct Of Preclinical And Proof Of Concept Studies In AES/MND Models). 2007. Guidelines for the preclinical in vivo evaluation of pharmacological active drugs for ALS/MND: Report on the 142nd ENMC international workshop. *Amyotrophic Lateral Sclerosis* 8: 217-223.) There were 15 mice in the placebo group. There were 16 mice in the S-oxprenolol group.

The primary endpoint was survival, humanely defined as the ability of the animal to right itself in 30 seconds after being laid on its side. Secondary endpoints were body weight, body composition, spontaneous activity and food intake. Body weight of the animals was assessed weekly until onset of disease. Additionally, body composition (fat mass and lean body mass) was assessed using NMR scans (EchoMRI-100, Echo Medical Systems, Houston, USA) every 4 days. After onset of disease, body weight and body composition were assessed every two days until the end of the study. All personal handling the animals was strictly blinded to the randomized treatment allocation.

Example 4

Effect of S-Oxprenolol on Survival

Figure 2:
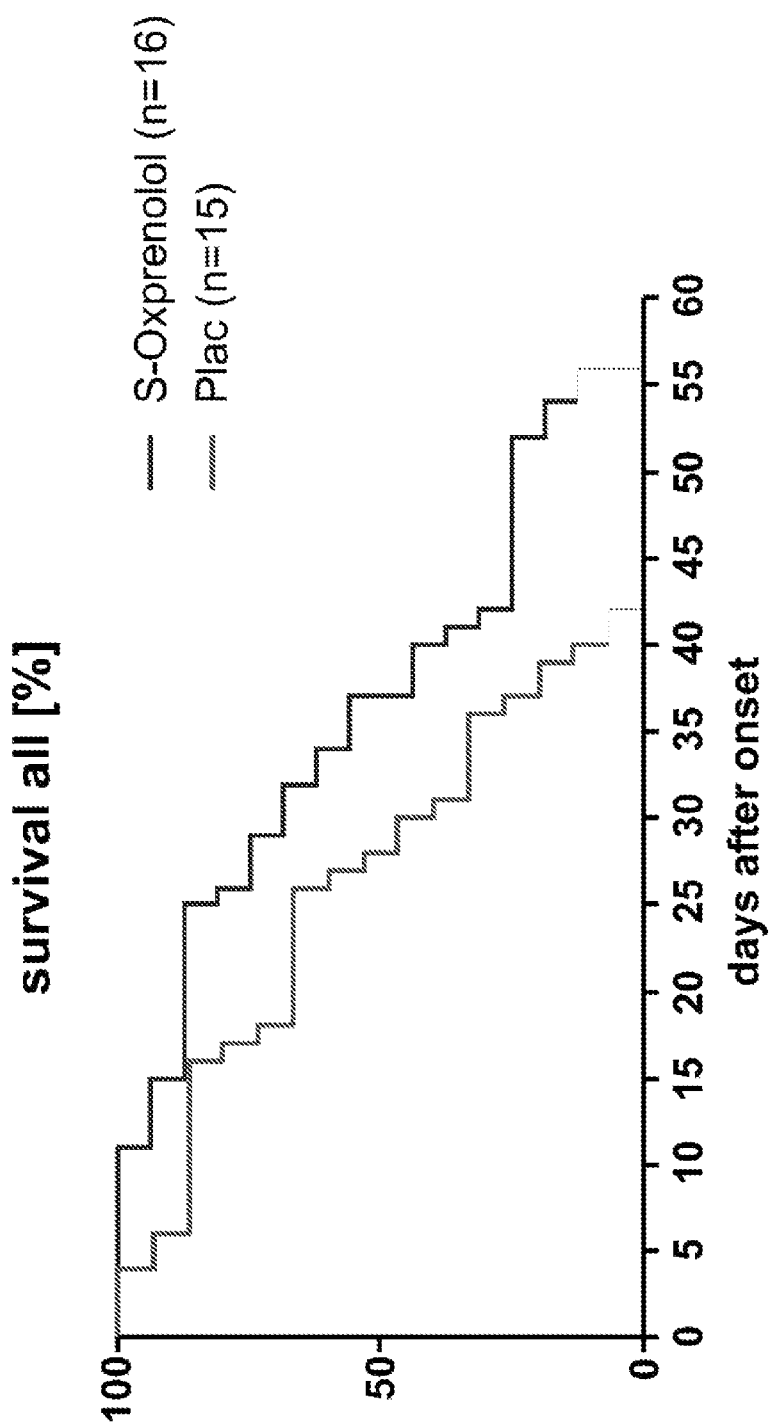
FIG. 2 is a graph showing the percent survival of mice populations that were administered with S-oxprenolol or a placebo (plac). The sample size in the population is indicated by "n."

To study the effect of S-oxprenolol on survival, survival was monitored over time. FIG. 2 shows the percent survival of mice that were administered with S-oxprenolol at dosages of 10 mg/kg/day. As shown in FIG. 2, mice receiving S-oxprenolol had longer survival than those in the placebo group. Treatment of G93A mice with 10 mg/kg/day of S-oxprenolol after onset of ALS significantly improved survival by about 33% compared to placebo treated mice (56 vs 42 days after onset, respectively, HR: 0.39, 95%CI: 0.171-0.88, p=0.0241, FIG. 2). Median survival was improved from 28 days (placebo) to 37 days (S-oxprenolol, ratio: 1.32, 95% CI:0.83-1.81).

Figure 3:
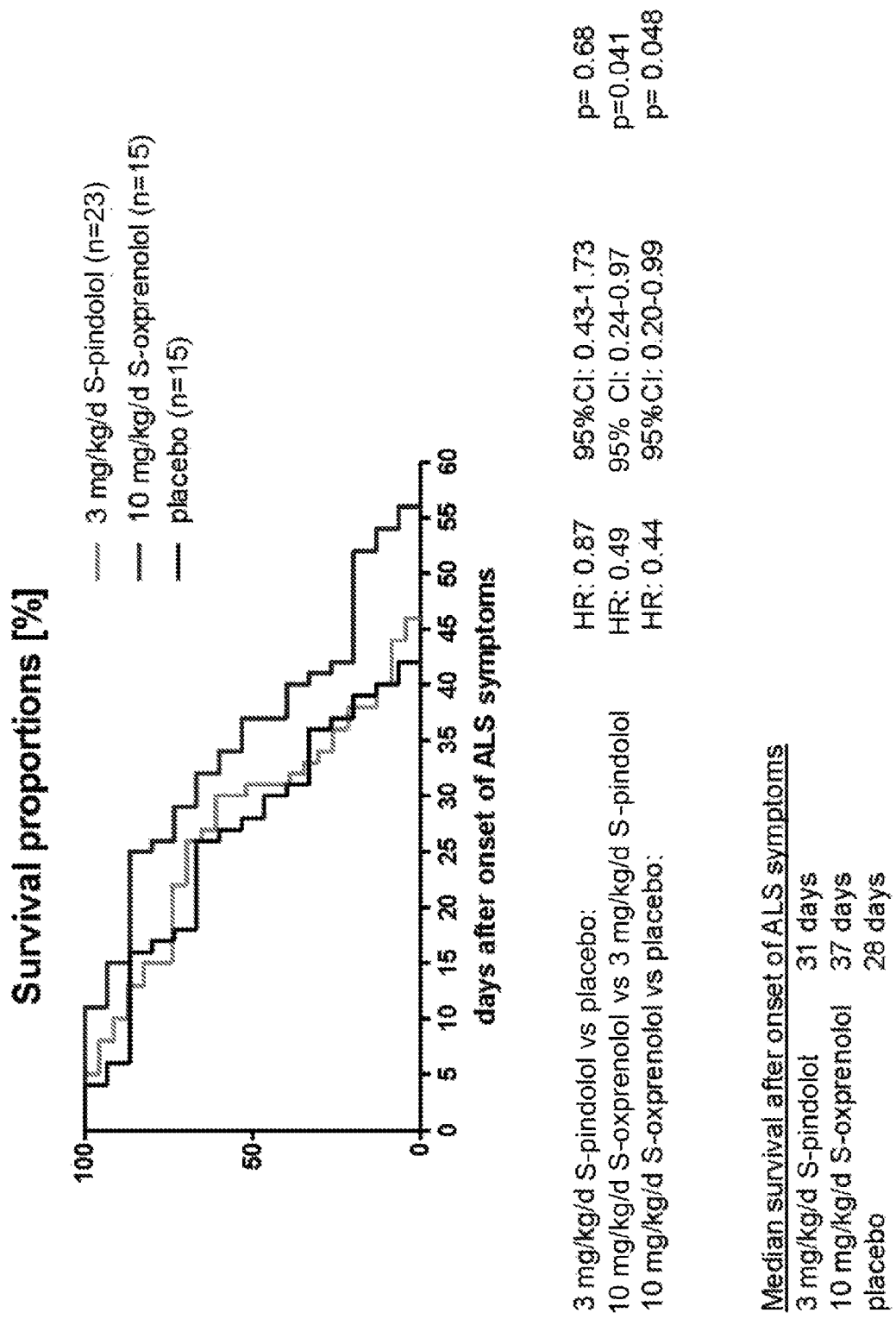
FIG. 3 is a graph showing the percent survival of mice populations that were administered S-oxprenolol, S-pindolol, or a placebo. The sample size in the population is indicated by "n." "HR" refers to hazard ratio. "CI" refers to confidence interval. "95% CI" is 95% confidence interval. "p" refers to p-value.

FIG. 3 shows the percent survival of mice that were administered S-oxprenolol at a dosage of 10 mg/kg/day. One control group received S-pindolol at its preferred dosage of 3 mg/kg/day. As shown in FIG. 3, S-oxprenolol was significantly superior to either placebo or S-pindolol at its preferred dose. The median survival after onset of ALS symptoms was 28 days for the placebo group; 31 days for the S-pindolol group; and 37 days for the S-oxprenolol group.

Figure 4:
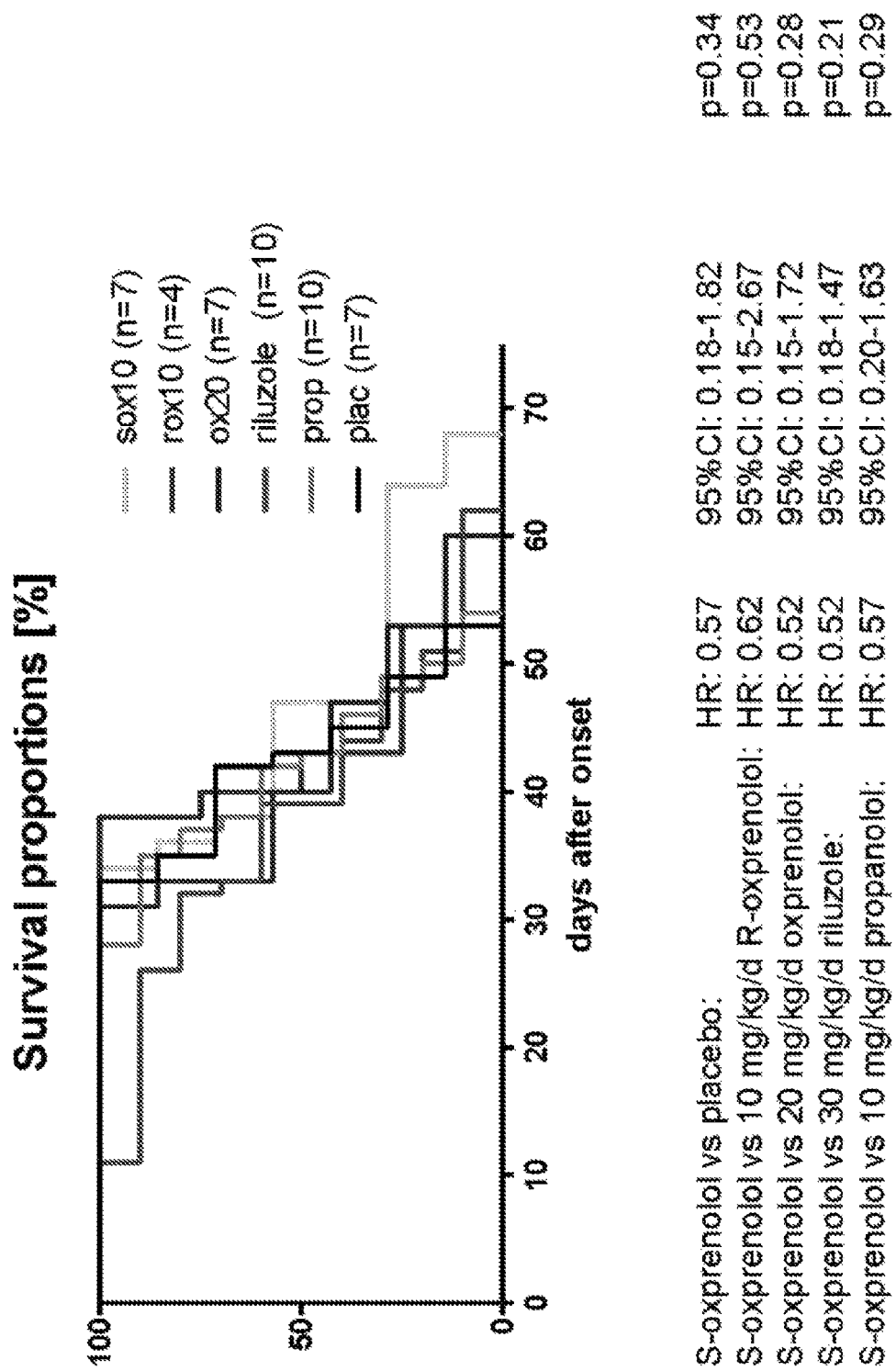
FIG. 4 is a graph showing the percent survival of mice populations that were administered S-oxprenolol (sox10), R-oxprenolol (rox10), oxprenolol (ox20). riluzole (riluzole), propanolol (prop), or a placebo (plac). The sample size in the population is indicated by "n." "HR" refers to hazard ratio. "CI" refers to confidence interval. "95% CI" is 95% confidence interval. "p" refers to p-value.

FIG. 4 shows the percent survival of mice that were administered S-oxprenolol at a dosage of 10 mg/kg/day, R-oxprenolol at a dosage of 10 mg/kg/day, oxprenolol at a dosage of 20 mg/kg/day, riluzole at a dosage of 30 mg/kg/day, or propanolol at a dosage of 10 mg/kg/day. There was also a placebo group. As shown in FIG. 4, S-oxprenolol was significantly superior to either placebo or the other compounds.

Example 5

Effect of S-Oxprenolol on Body Weight

To study the effect of S-oxprenolol on body weight, body weight was monitored over time.

Figure 5:
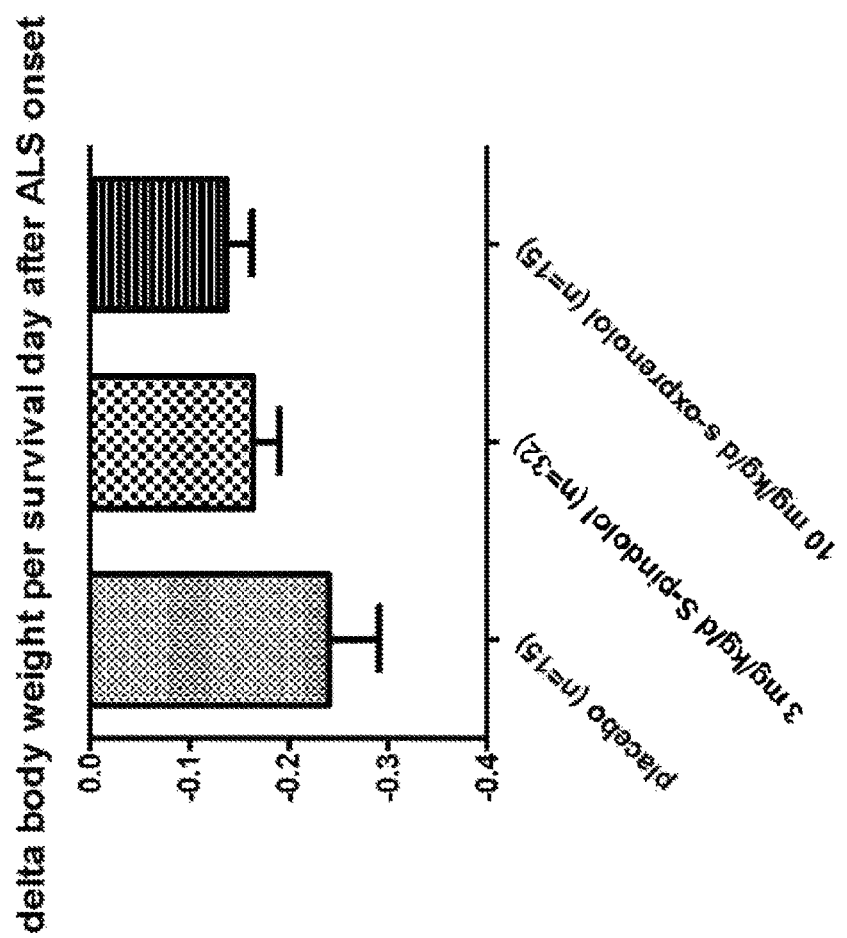
FIG. 5 is a graph showing the change in body weight per survival day after ALS onset of mice populations that were administered with various dosages of the S-oxprenolol, S-pindolol, or a placebo. The sample size in the population is indicated by "n."

FIG. 5 shows the change of body weight (in grams per day alive after onset of ALS symptoms) per survival day after ALS onset in mice administered S-oxprenolol at a dosage of 10 mg/kg/day or S-pindolol at preferred dosage of 3 mg/kg/day. As shown in FIG. 5, mice receiving S-oxprenolol had body weight loss that was close to those administered S-pindolol. Mice receiving S-oxprenolol had less body weight loss than those in the placebo group.

Example 6

Effects of S-Oxprenolol on Preserving Lean Body Mass

To study the effect of the test compounds on lean body mass, lean mass was determined at the end of the study.

Figure 6:
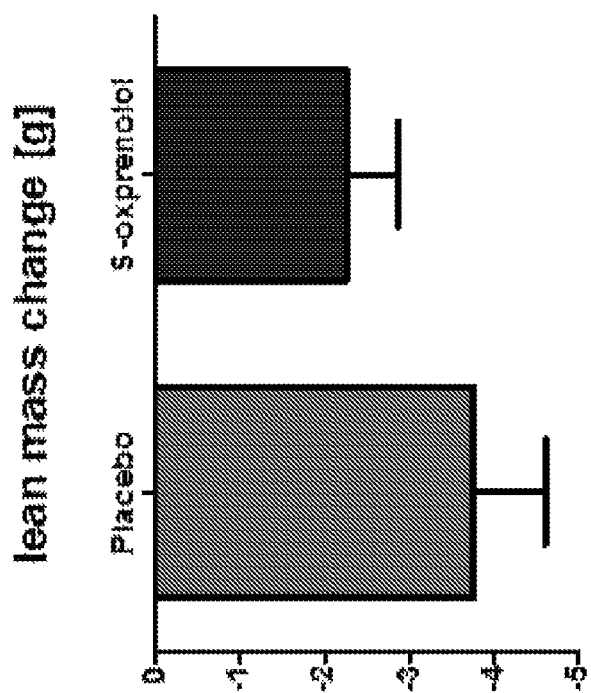
FIG. 6 is a graph showing the change in lean body mass (in grams ("g")) of mice populations that were administered with S-oxprenolol or a placebo.

In this experiment, all mice were killed using the 30 seconds endpoint and hence all mice were equally diseased at the end of the study. FIG. 6 shows the change in lean body mass (in grains) of mice that were administered S-oxprenolol at a dosage of 10 mg/kg/day. As shown in FIG. 6, rats receiving S-oxprenolol had less change in lean body mass than those receiving a placebo. Wasting of lean mass was reduced by about 40% by active treatment compared to placebo (p=0.18, FIG. 6). This effect shows that S-oxprenolol is effective in preserving lean body mass.

Figure 7:
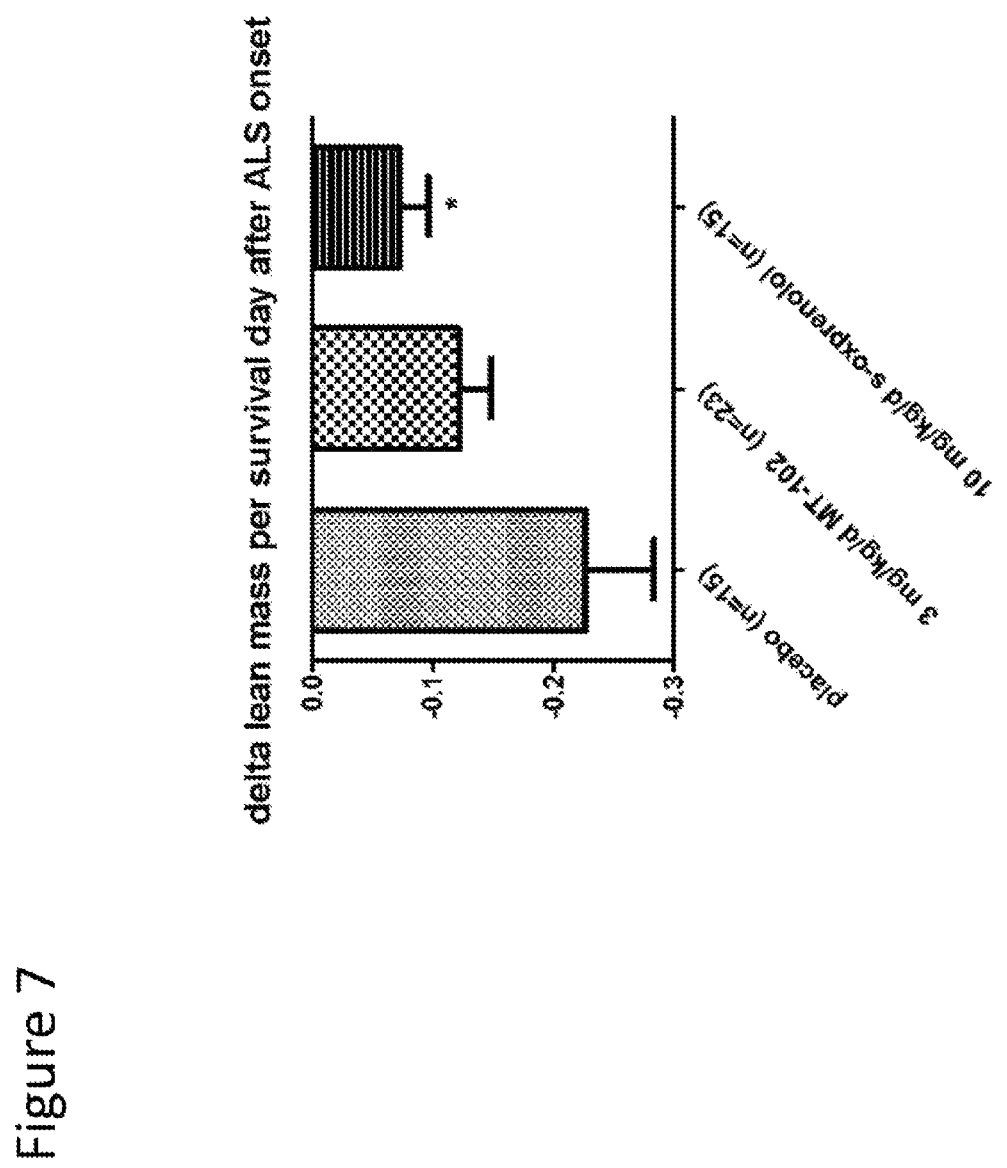
FIG. 7 is a graph showing the change in lean body mass per survival day after ALS onset of mice populations that were administered with S-oxprenolol, S-pindolol, or a placebo. The asterisk (*) indicates that the p value is less than 0.05 versus placebo.

FIG. 7 shows the change in lean body mass (in grams per day alive after onset of ALS symptoms) per survival day after ALS onset of mice that were administered S-oxprenolol at a dosage of 10 mg/kg/day or S-pindolol at preferred dosage of 3 mg/kg/day. As shown in FIG. 6, rats receiving S-oxprenolol had less change in lean body mass than those receiving S-pindolol.

Example 7

Effects of S-Oxprenolol on Skeletal Muscle Atrophy

To study the effect of the test compounds on skeletal muscle atrophy, the skeletal muscle mass were determined at the end of the study.

Figure 8:
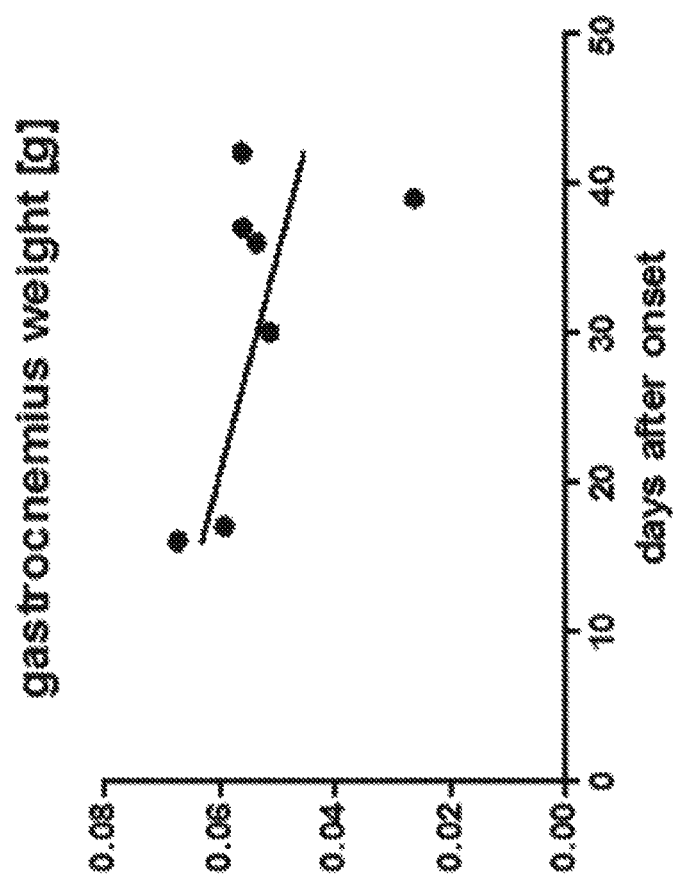
FIG. 8 is a graph showing the mass of gastrocnemius muscle (in grams ("g")) in mice populations that were administered a placebo.
Figure 9:
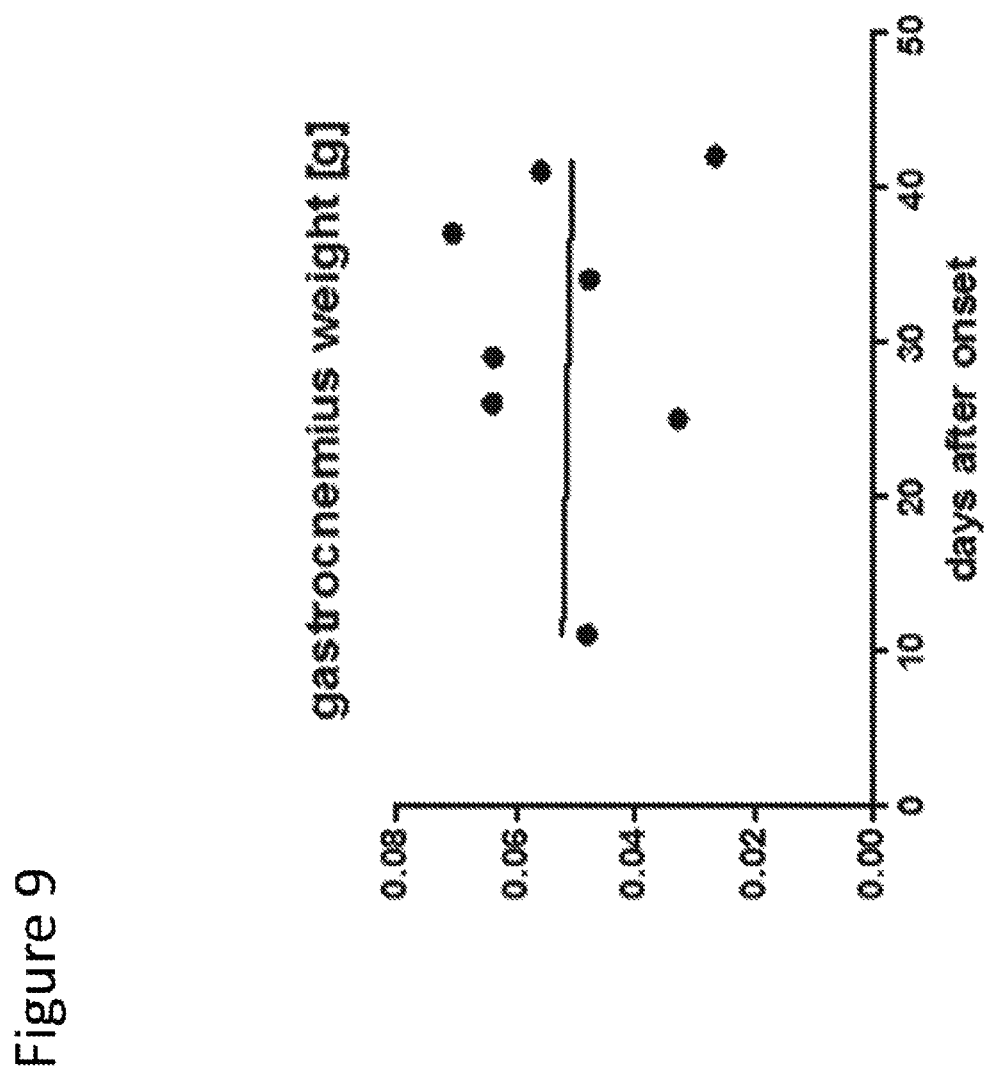
FIG. 9 is a graph showing the mass of gastrocnemius muscle (in grams ("g")) in mice populations that were administered S-oxprenolol.

FIGS. 8-11 show the mass of various types of skeletal muscle (in grams) of mice populations that were administered S-oxprenolol at a dosage of 10 mg/kg/day or a placebo. FIG. 8 shows results for gastrocnemius muscle weight plotted with days after onset for the placebo group. A trend for a correlation of days after onset (=survival) and gastrocnemius weight was seen in placebo-treated mice. (R:–0.56, p=0.18) FIG. 9 shows results for gastrocnemius muscle weight plotted with days after onset for the S-oxprenolol group. FIG. 9 shows that with administration of S-oxprenolol, the gastrocnemius weight in the G93A ALS model is steady. There is no correlation of days after onset (=survival) for gastrocnemius weight. (R:–0.03, p-0.94)

Figure 10:
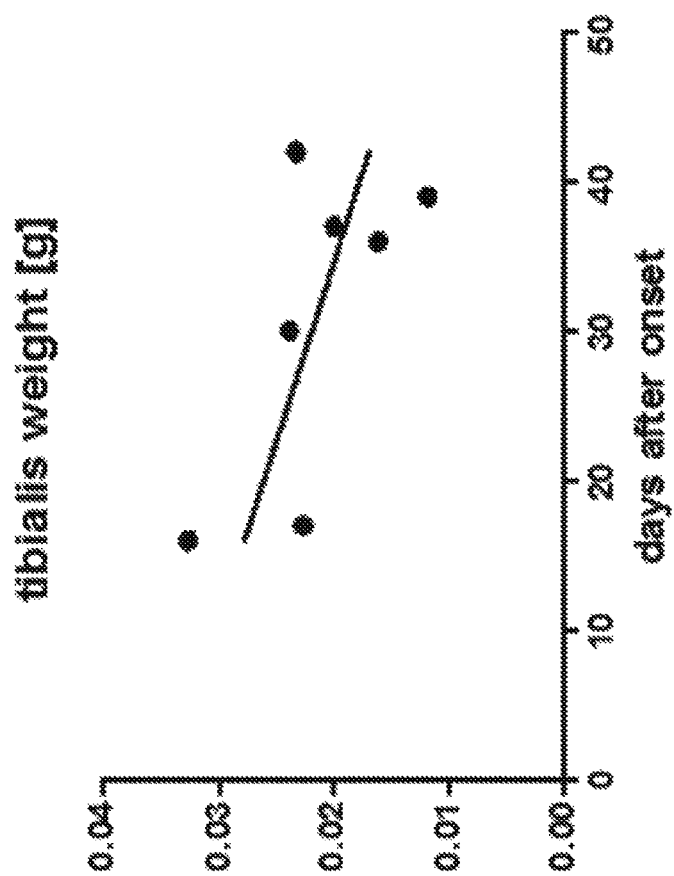
FIG. 10 is a graph showing the mass of tibialis anterior muscle (in grams ("g")) in mice populations that were administered a placebo.
Figure 11:
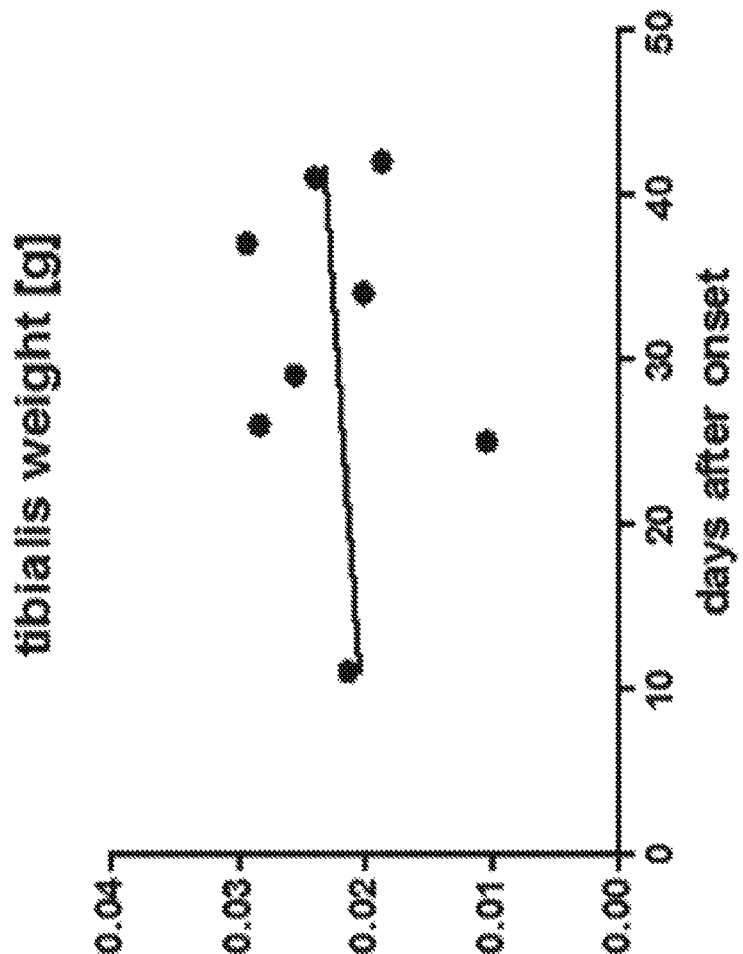
FIG. 11 is a graph showing the mass of tibialis anterior muscle (in grams ("g")) in mice populations that were administered S-oxprenolol.

FIG. 10 shows results for tibialis anterior muscle weight plotted with days after onset for the placebo group. A trend for a correlation of days after onset (=survival) and tibialis anterior muscle weight was seen in placebo-treated mice. (R:–0.67, p=0.097) FIG. 11 shows results for tibialis anterior muscle weight plotted with days after onset for the S-oxprenolol group. FIG. 11 shows that with administration of S-oxprenolol, the tibialis anterior muscle weight in the G93A ALS model is steady. There is no correlation of days after onset (=survival) for tibialis anterior muscle. (R:0.15, p=0.72)

The loss of mass of the mixed-fiber type muscle gastrocnemius showed a trend for a correlation of survival (=days after onset of disease, FIG. 8), while mice treated with S-oxprenolol (FIG. 9) showed no correlation, indicating a muscle protective role of S-oxprenolol. The loss of mass of the mixed-fiber type muscle tibialis showed a strong trend for a correlation of survival (=days after onset of disease, FIG. 10), while mice treated with S-oxprenolol showed no correlation (FIG. 11), again indicating a muscle protective role of S-oxprenolol.

Example 8

Effects of S-Oxprenolol on Preserving Fat Mass

To study the effect of the test compounds on fat mass, the fat mass were determined at the end of the study.

Figure 12:
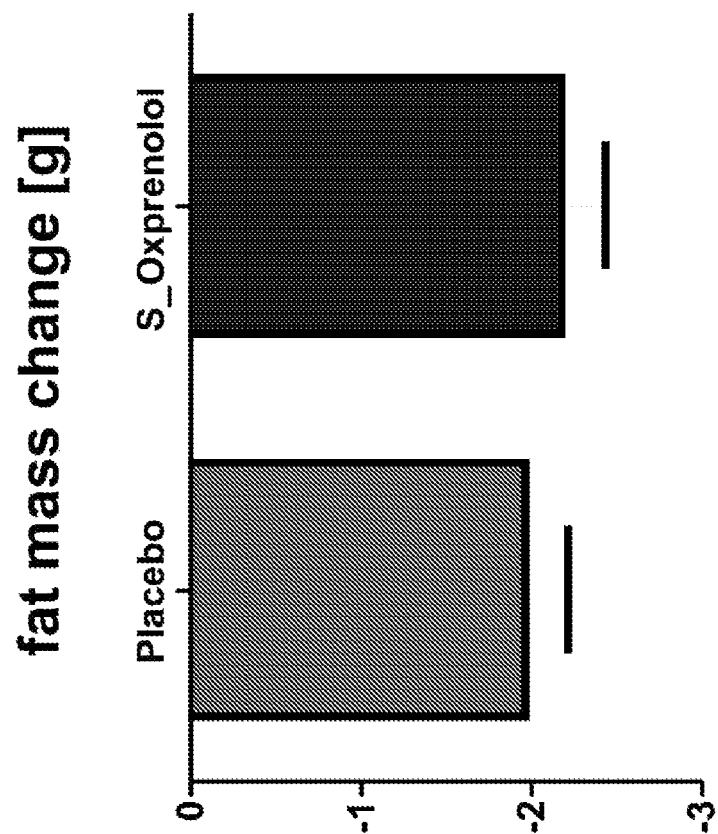
FIG. 12 is a graph showing the change in fat mass (in grams ("g")) of mice populations that were administered S-oxprenolol or a placebo.

FIG. 12 shows the change in fat mass (in grams) of mice administered S-oxprenolol. As shown in FIG. 12, rats receiving S-oxprenolol had no reduction in fat mass than those in the placebo group. S-oxprenolol had no effect on the loss of fat mass (p>0.5, FIG. 12).

Figure 13:
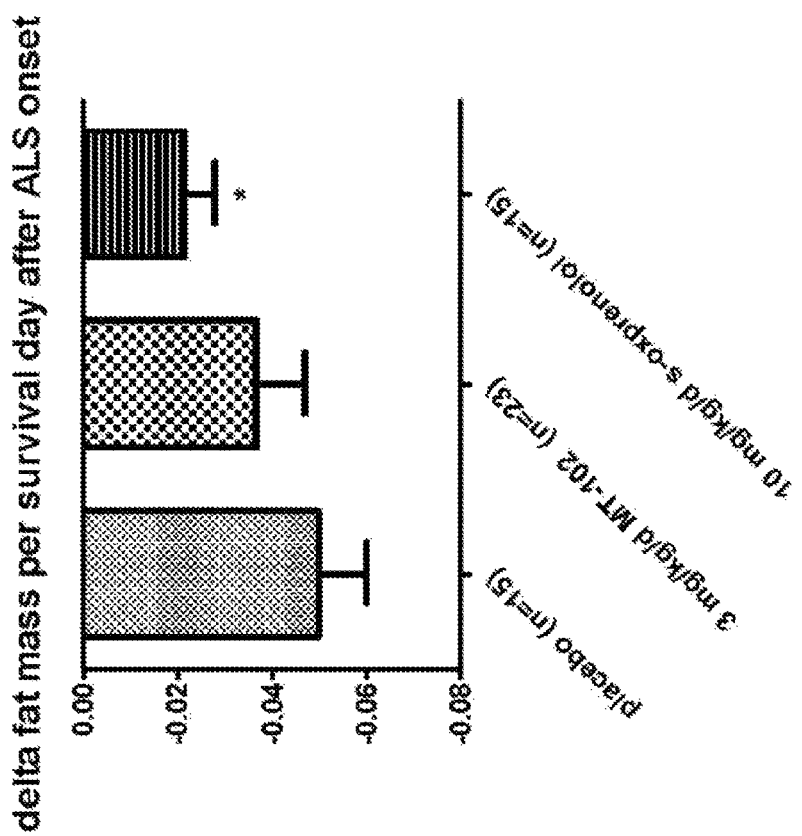
FIG. 13 is a graph showing the change in fat mass per survival day after ALS onset of mice populations that were administered with S-oxprenolol, S-pindolol, or a placebo. The asterisk (*) indicates that the p value is less than 0.05 versus placebo.

FIG. 13 shows the change in fat mass (in grams per day alive after onset of ALS symptoms) per survival day after ALS onset of mice that were administered S-oxprenolol at a dosage of 10 mg/kg/day or S-pindolol at preferred dosage of 3 mg/kg/day. As shown in FIG. 13, rats receiving S-oxprenolol had less change in fat mass than those receiving S-pindolol.

The difference between FIGS. 12 and 13 is explained by the survival. The overall loss of fat mass is equal on the day the animals are euthanized. But mice treated with S-oxprenolol lived longer and therefore the loss of fat mass per day alive after onset of ALS symptoms is lower (=overall fat loss divided by number of days alive after ALS onset).

Example 9

Effects of S-Oxprenolol on Improving Outcome of ALS Compared to R-Oxprenolol and Rilutek To study the effect of S-oxprenolol on survival compared to R-oxprenolol and rilutek, survival was monitored over time. Rilutek (Riluzole, structure shown below) is used for treating ALS.

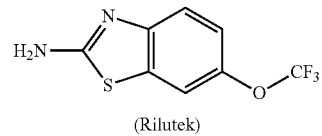 [SMILES: Nc1nc2ccc(OC(F)(F)F)cc2s1]

(Rilutek)

Figure 14:
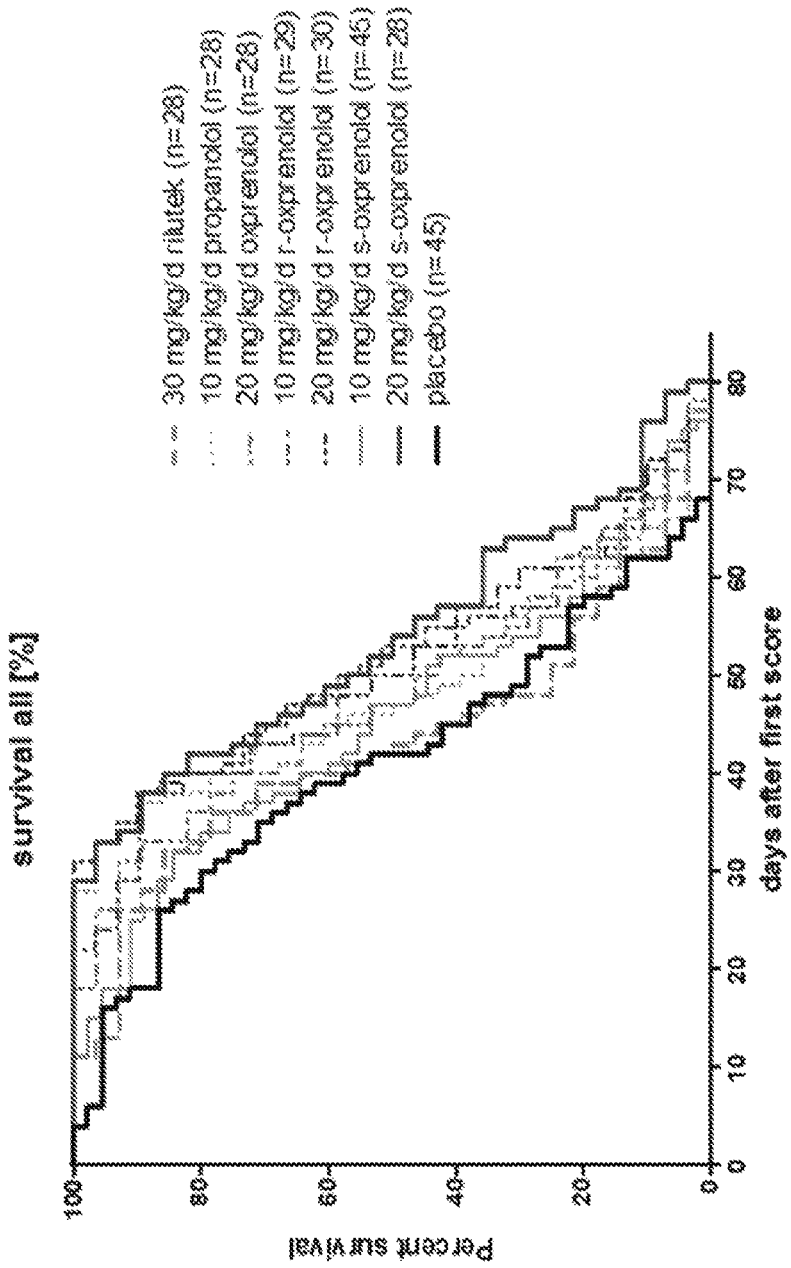
FIG. 14 is a graph showing the percent survival of mice populations that were administered with S-oxprenolol, rilutek, propanolol, oxprenolol (racemic), or R-oxprenolol. The sample size in the population is indicated by "n."

FIG. 14 shows the percent survival of mice that were administered with S-oxprenolol at dosages of 10 mg/kg/day or 20 mg/kg/day. Other groups of mice were administered rilutek at a dosage of 30 ma/kg/day; propanolol at a dosage of 10 mg/kg/day; oxprenolol (racemic) at a dosage of 20 mg/kg/day; R-oxprenolol at a dosage of 10 mg/kg/day or 20 mg/kg/day; or a placebo. The number of mice in each population is indicated as "n" in FIG. 14. As shown in FIG. 14, mice receiving S-oxprenolol at a dosage of 20 mg/kg/day had longer survival than other groups.

The statistical data for FIG. 14 is shown below. "HR" refers to hazard ratio. "95% CI" is confidence interval. "p" refers to p value.

TABLE 1

Statistical data for FIG. 14 (for all mice)

| Comparison (dosage in mg/kg/day) | HR | 95% CI | p value |
|---|---|---|---|
| Rilutek (30) vs. placebo | 0.89 | 0.55-1.46 | 0.65 |
| Propanolol (10) vs. placebo | 0.73 | 0.45-1.18 | 0.20 |
| Oxprenolol (20) vs. placebo | 0.66 | 0.40-1.07 | 0.09 |
| R-Oxprenolol (10) vs. placebo | 0.57 | 0.35-0.93 | 0.0227 |
| R-Oxprenolol (20) vs. placebo | 0.54 | 0.34-0.88 | 0.013 |
| S-Oxprenolol (10) vs. placebo | 0.71 | 0.46-1.10 | 0.13 |
| S-Oxprenolol (20) vs. placebo | 0.45 | 0.27-0.73 | 0.0014 |
| Rilutek (30) vs. S-Oxprenolol (20) | 2.07 | 1.17-3.67 | 0.0129 |
| Propanolol (10) vs. S-Oxprenolol (10) | 1.06 | 0.65-1.74 | 0.82 |
| Propanolol (10) vs. S-Oxprenolol (20) | 1.77 | 0.99-3.15 | 0.0532 |
| R-Oxprenolol (20) vs. S-Oxprenolol (20) | 1.32 | 0.77-2.28 | 0.31 |
| S-Oxprenolol (20) vs. placebo | 0.45 | 0.27-0.73 | 0.0014 |

Figure 15:
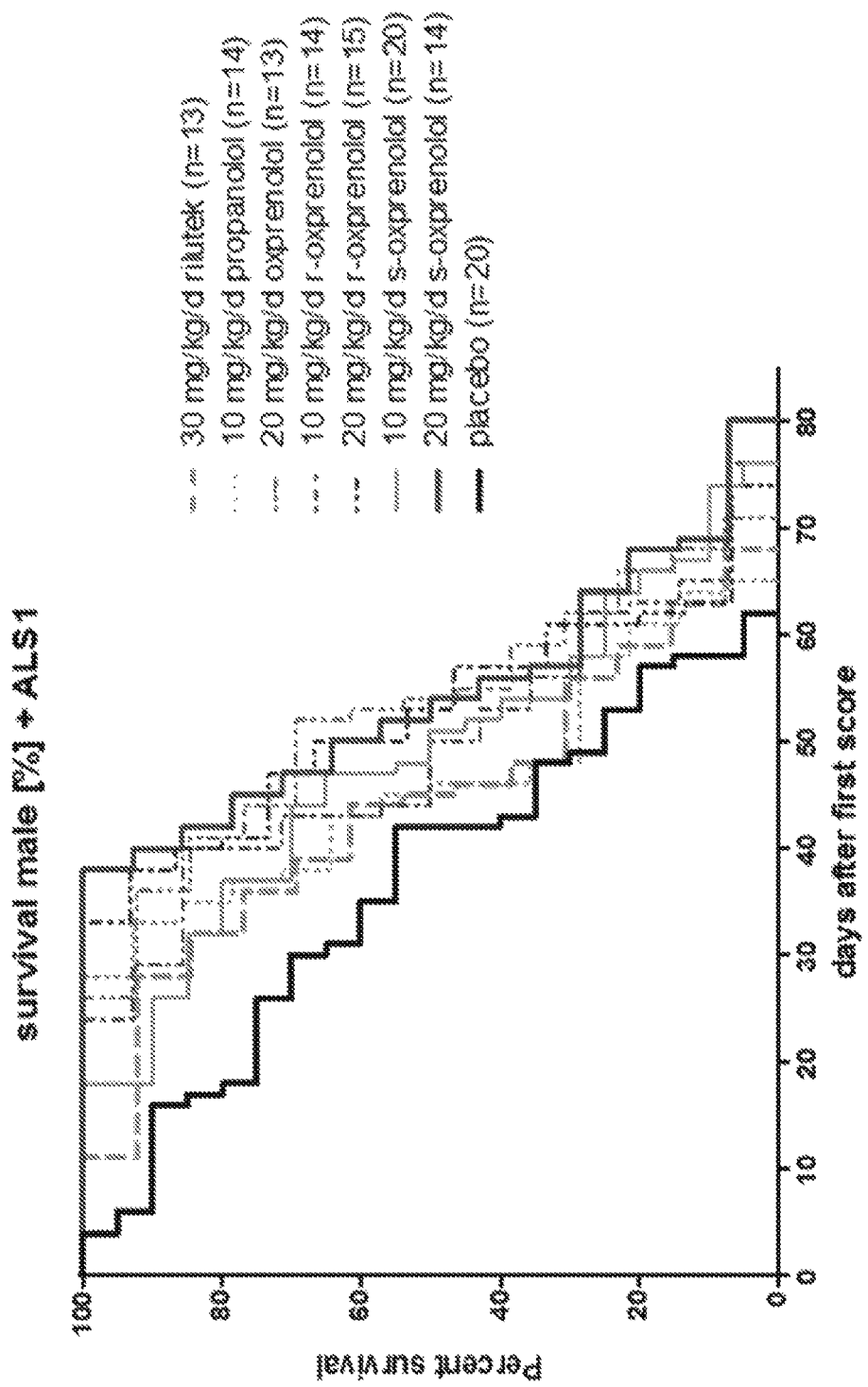
FIG. 15 is a graph showing the percent survival of male mice populations that were administered with S-oxprenolol, rilutek, propanolol, oxprenolol (racemic), or R-oxprenolol. The sample size in the population is indicated by "n."

FIG. 15 shows the percent survival of male mice that were administered with S-oxprenolol at dosages of 10 mg/kg/day or 20 mg/kg/day. Other groups of male mice were administered rilutek at a dosage of 30 mg/kg/day; propanolol at a dosage of 10 mg/kg/day; oxprenolol (racemic) at a dosage of 20 mg/kg/day; R-oxprenolol at a dosage of 10 mg/kg/day or 20 mg/kg/day; or a placebo. The number of male mice in each population is indicated as "n" in FIG. 15. As shown in FIG. 15. male mice receiving S-oxprenolol at a dosage of 20 mg/kg/day had longer survival than other groups.

The statistical data for FIG. 15 is shown below. "HR" refers to hazard ratio. "95° A CI" is confidence interval. "p" refers to p value.

TABLE 2

Statistical data for FIG. 15 (for male mice)

| Comparison (dosage in mg/kg/day) | HR | 95% CI | p value |
|---|---|---|---|
| Rilutek (30) vs. placebo | 0.63 | 0.30-1.29 | 0.21 |
| Propanolol (10) vs. placebo | 0.59 | 0.29-1.21 | 0.15 |
| Oxprenolol (20) vs. placebo | 0.38 | 0.18-0.80 | 0.0114 |
| R-Oxprenolol (10) vs. placebo | 0.49 | 0.23-0.99 | 0.0492 |
| R-Oxprenolol (20) vs. placebo | 0.41 | 0.19-0.86 | 0.0176 |
| S-Oxprenolol (10) vs. placebo | 0.46 | 0.23-0.92 | 0.0289 |
| S-Oxprenolol (20) vs. placebo | 0.39 | 0.19-0.83 | 0.0139 |
| Rilutek (30) vs. S-Oxprenolol (20) | 1.96 | 0.85-4.51 | 0.11 |
| Propanolol (10) vs. S-Oxprenolol (10) | 1.64 | 0.75-3.48 | 0.22 |
| Propanolol (10) vs. S-Oxprenolol (20) | 1.98 | 0.88-4.49 | 0.099 |
| R-Oxprenolol (20) vs. S-Oxprenolol (20) | 1.24 | 0.57-2.69 | 0.58 |
| S-Oxprenolol (20) vs. placebo | 0.39 | 0.19-0.83 | 0.0139 |

Figure 16:
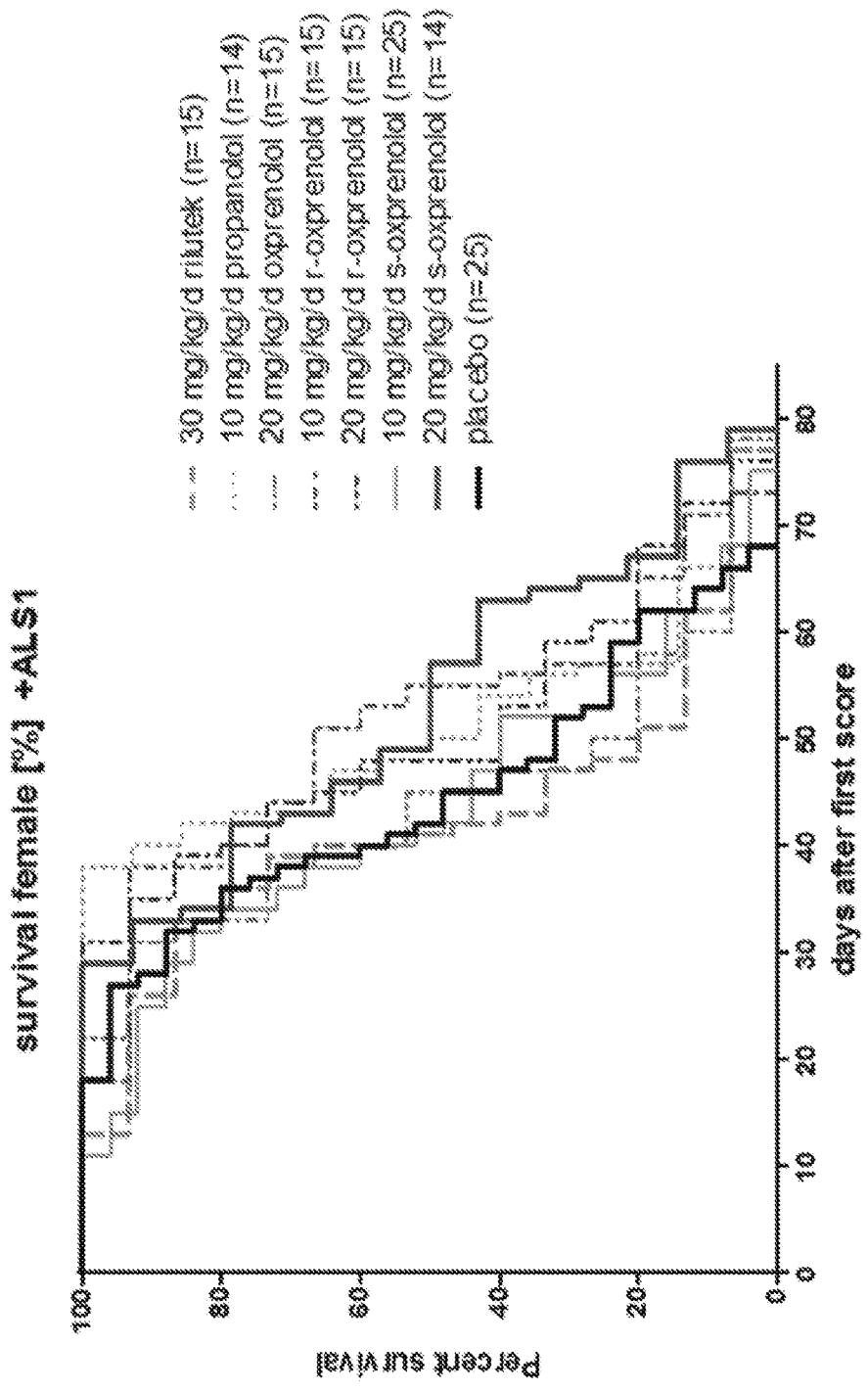
FIG. 16 is a graph showing the percent survival of female mice populations that were administered with S-oxprenolol, rilutek, propanolol, oxprenolol (racemic), or R-oxprenolol. The sample size in the population is indicated by "n."

FIG. 16 shows the percent survival of female mice that were administered with S-oxprenolol at dosages of 10 mg/kg/day or 20 mg/kg/day. Other groups of female mice were administered rilutek at a dosage of 30 mg/kg/day; propanolol at a dosage of 10 mg/kg/day; oxprenolol (racemic) at a dosage of 20 mg/kg/day; R-oxprenolol at a dosage of 10 mg/kg/day or 20 mg/kg/day; or a placebo. The number of female mice in each population is indicated as "n" in FIG. 16. As shown in FIG. 16, female mice receiving S-oxprenolol at a dosage of 20 mg/kg/day had longer survival than other groups.

The statistical data for FIG. 16 is shown below. "HR" refers to hazard ratio. "95% CI" is confidence interval. "p" refers to p value.

TABLE 3

Statistical data for FIG. 16 (for female mice)

| Comparison (dosage in mg/kg/day) | HR | 95% CI | p value |
|---|---|---|---|
| Rilutek (30) vs. placebo | 1.08 | 0.55-2.15 | 0.82 |
| Propanolol (10) vs. placebo | 0.71 | 0.36-1.39 | 0.32 |
| Oxprenolol (20) vs. placebo | 1.03 | 0.52-2.02 | 0.94 |
| R-Oxprenolol (10) vs. placebo | 0.60 | 0.31-1.15 | 0.13 |
| R-Oxprenolol (20) vs. placebo | 0.41 | 0.31-1.16 | 0.13 |
| S-Oxprenolol (10) vs. placebo | 0.96 | 0.53-1.73 | 0.89 |
| S-Oxprenolol (20) vs. placebo | 0.53 | 0.27-1.02 | 0.058 |
| Rilutek (30) vs. S-Oxprenolol (20) | 2.04 | 0.92-4.51 | 0.077 |
| Propanolol (10) vs. S-Oxprenolol (10) | 0.75 | 0.38-1.46 | 0.39 |
| Propanolol (10) vs. S-Oxprenolol (20) | 1.49 | 0.67-3.34 | 0.32 |
| R-Oxprenolol (20) vs. S-Oxprenolol (20) | 1.26 | 0.59-2.72 | 0.55 |
| S-Oxprenolol (20) vs. placebo | 0.53 | 0.27-1.02 | 0.058 |

Figure 17:
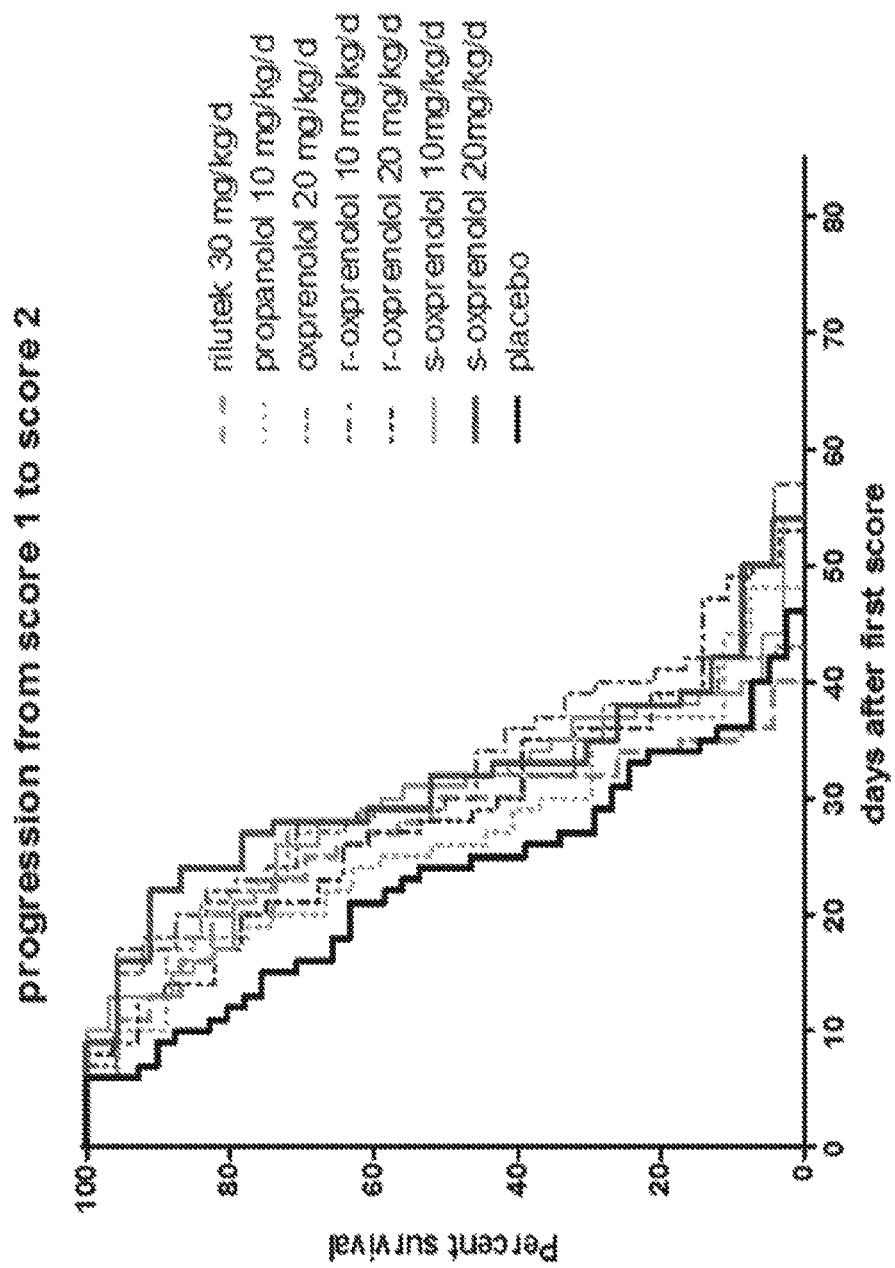
FIG. 17 is a graph showing the change in disease progression scored from score 1 to score 2 of mice populations that were administered with S-oxprenolol, rilutek, propanolol, oxprenolol (racemic), or R-oxprenolol.
Figure 18:
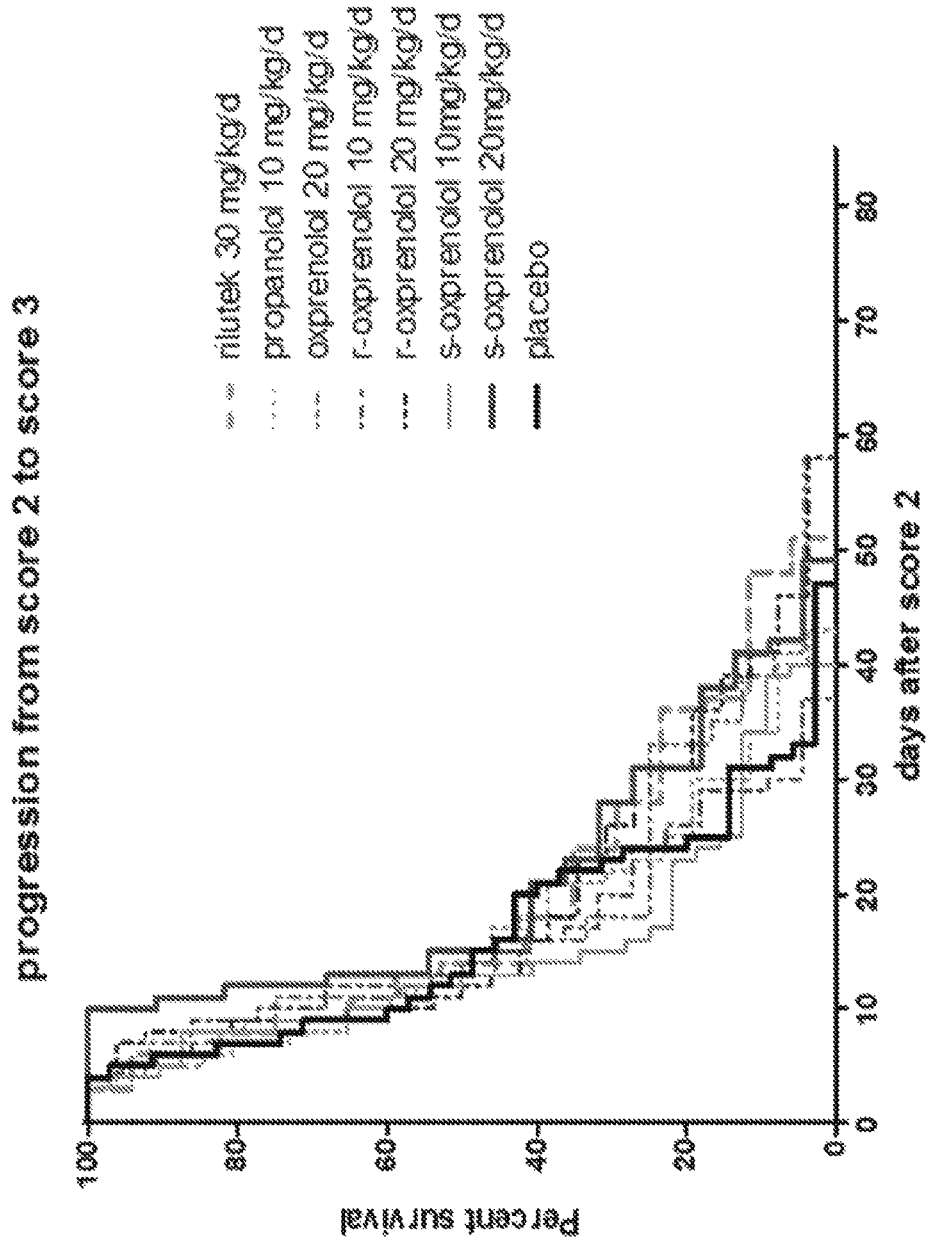
FIG. 18 is a graph showing the change in disease progression scored from score 2 to score 3 of mice populations that were administered with S-oxprenolol, rilutek, propanolol, oxprenolol (racemic), or R-oxprenolol.
Figure 19:
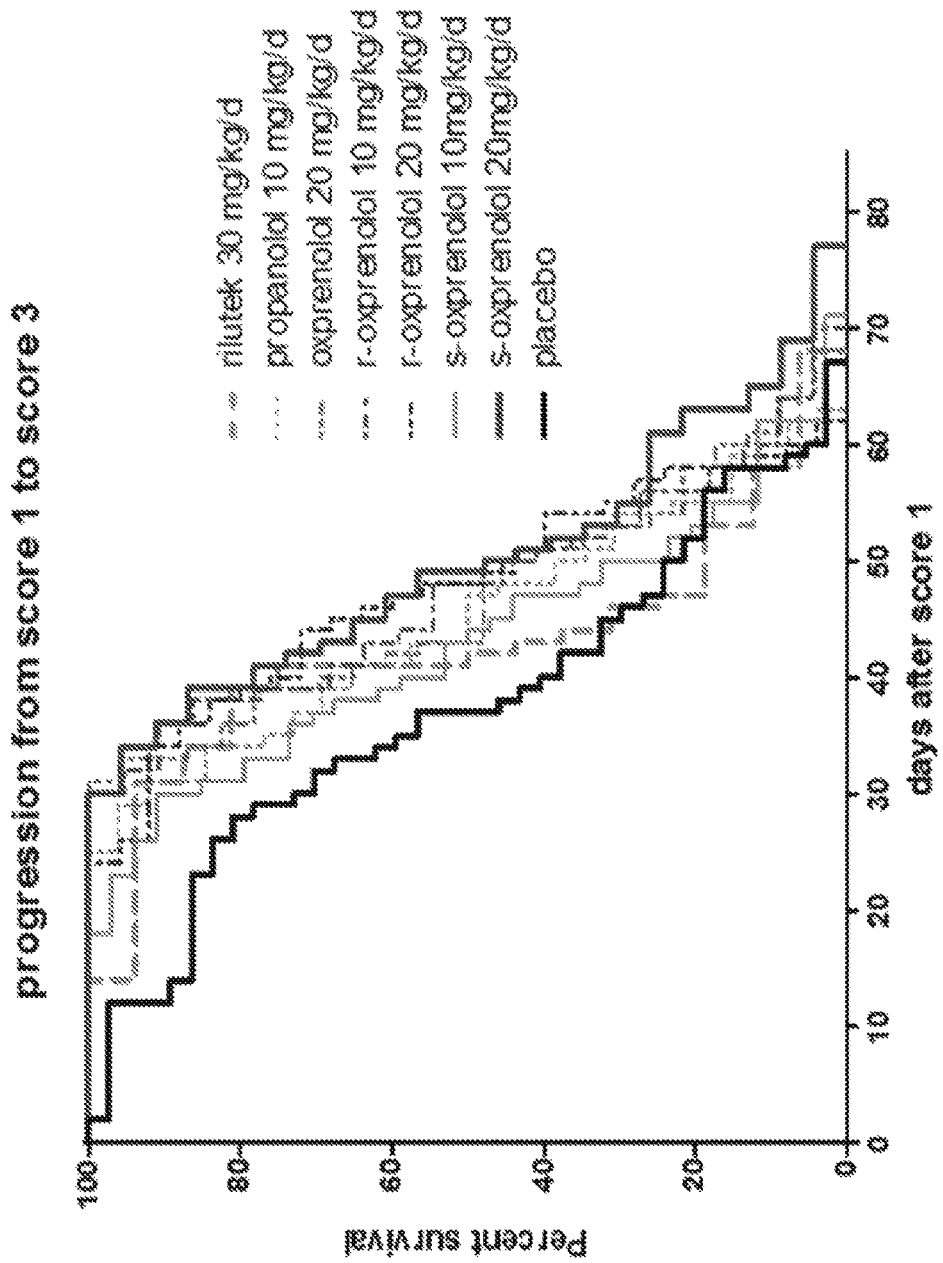
FIG. 19 is a graph showing the change in disease progression scored from score 1 to score 3 of mice populations that were administered with S-oxprenolol, rilutek, propanolol, oxprenolol (racemic), or R-oxprenolol.

FIGS. 17-19 show changes in disease progression of scores in tested mice. The disease progression score is based on the JAX SOP (Ludolph A C, Bendotti C, Blaugrund E, Hengerer B, Loffler J P, Martin J, Meininger V, Meyer T, Moussaoui S, Robberecht W, Scott S, Silani V, Van Den Berg L H (ENMC Group For The Establishment Of Guidelines For The Conduct Of Preclinical And Proof Of Concept Studies In ALS/MND Models). 2007, which is incorporated by reference).

FIG. 17 shows the percent of mice that improved from disease progression of score 1 to score 2 that were administered with S-oxprenolol at dosages of 10 mg/kg/day or 20 mg/kg/day. Other groups of mice were administered rilutek at a dosage of 30 mg/kg/day; propanolol at a dosage of 10 mg/kg/day; oxprenolol (racemic) at a dosage of 20 mg/kg/day; R-oxprenolol at a dosage of 10 mg/kg/day or 20 mg/kg/day; or a placebo.

The statistical data for FIG. 17 is shown below. "HR" refers to hazard ratio. "95% CI" is confidence interval. "p" refers to p value.

TABLE 4

Statistical data for FIG. 17 (Progression from score 1 to score 2)

| Comparison (dosage in mg/kg/day) | HR | 95% CI | p value |
|---|---|---|---|
| Rilutek vs. placebo | 0.82 | 0.48-1.40 | 0.47 |
| Propanolol vs. placebo | 0.64 | 0.39-1.06 | 0.086 |
| Oxprenolol vs. placebo | 0.60 | 0.36-1.01 | 0.053 |
| R-Oxprenolol (10) vs. placebo | 0.47 | 0.28-0.79 | 0.0047 |
| R-Oxprenolol (20) vs. placebo | 0.54 | 0.32-0.90 | 0.0176 |
| S-Oxprenolol (10) vs. placebo | 0.56 | 0.35-0.91 | 0.0189 |
| S-Oxprenolol(20) vs. placebo | 0.51 | 0.31-0.87 | 0.0128 |
| Rilutek vs. S-Oxprenolol (10) | 1.68 | 0.92-3.08 | 0.093 |
| Rilutek vs. S-Oxprenolol (20) | 1.73 | 0.91-3.29 | 0.094 |
| Propanolol vs. S-Oxprenolol (10) | 1.27 | 0.73-2.21 | 0.39 |
| Propanolol vs. S-Oxprenolol (20) | 1.49 | 0.82-2.69 | 0.19 |
| R-Oxprenolol (10) vs. S-Oxprenolol (10) | 0.73 | 0.42-1.27 | 0.27 |
| S-Oxprenolol (20) vs. S-Oxprenolol (20) | 1.17 | 0.65-2.09 | 0.60 |

FIG. 18 shows the percent of mice that improved from disease progression of score 2 to score 3 that were administered with S-oxprenolol at dosages of 10 mg/kg/day or 20 mg/kg/day. Other groups of mice were administered rilutek at a dosage of 30 mg/kg/day; propanolol at a dosage of 10 mg/kg/day; oxprenolol (racemic) at a dosage of 20 mg/kg/day; R-oxprenolol at a dosage of 10 mg/kg/day or 20 mg/kg/day; or a placebo.

The statistical data for FIG. 18 is shown below. "HR" refers to hazard ratio. "95% CI" is confidence interval. "p" refers to p value.

TABLE 5

Statistical data for FIG. 18 (Progression from score 2 to score 3)

| Comparison (dosage in mg/kg/day) | HR | 95% CI | p value |
|---|---|---|---|
| Rilutek vs. placebo | 0.68 | 0.37-1.24 | 0.21 |
| Propanolol vs. placebo | 0.99 | 0.58-1.69 | 0.97 |
| Oxprenolol vs. placebo | 0.77 | 0.44-1.33 | 0.35 |
| R-Oxprenolol (10) vs. placebo | 1.04 | 0.59-1.82 | 0.91 |
| R-Oxprenolol (20) vs. placebo | 0.74 | 0.43-1.27 | 0.27 |
| S-Oxprenolol (10) vs. placebo | 1.07 | 0.64-1.79 | 0.79 |
| S-Oxprenolol (20) vs. placebo | 0.64 | 0.37-1.12 | 0.12 |
| Rilutek vs. S-Oxprenolol (10) | 0.69 | 0.38-1.28 | 0.24 |
| Rilutek vs. S-Oxprenolol (20) | 1.06 | 0.54-2.06 | 0.87 |
| Propanolol vs. S-Oxprenolol (10) | 0.84 | 0.48-1.46 | 0.54 |
| Propanolol vs. S-Oxprenolol (20) | 1.46 | 0.81-2.64 | 0.21 |
| R-Oxprenolol (10) vs. S-Oxprenolol (10) | 0.95 | 0.53-1.69 | 0.87 |
| S-Oxprenolol (20) vs. S-Oxprenolol (20) | 1.20 | 0.66-2.19 | 0.55 |

FIG. 19 shows the percent of mice that improved from disease progression of score 1 to score 3 that were administered with S-oxprenolol at dosages of 10 mg/kg/day or 20 mg/kg/day. Other groups of mice were administered rilutek at a dosage of 30 mg/kg/day; propanolol at a dosage of 10 mg/kg/day; oxprenolol (racemic) at a dosage of 20 mg/kg/day; R-oxprenolol at a dosage of 10 mg/kg/day or 20 mg/kg/day; or a placebo.

The statistical data for FIG. 19 is shown below. "HR" refers to hazard ratio. "95% CI" is confidence interval. "p" refers to p value.

TABLE 6

Statistical data for FIG. 19 (Progression fromscore 1 to score 3)

| Comparison (dosage in mg/kg/day) | HR | 95% CI | p value |
|---|---|---|---|
| Rilutek vs. placebo | 0.76 | 0.42-1.37 | 0.84 |
| Propanolol vs. placebo | 0.72 | 0.43-1.21 | 0.21 |
| Oxprenolol vs. placebo | 0.60 | 0.35-1.01 | 0.055 |
| R-Oxprenolol (10) vs. placebo | 0.60 | 0.35-1.02 | 0.060 |
| R-Oxprenolol (20) vs. placebo | 0.63 | 0.37-1.07 | 0.086 |
| S-Oxprenolol (10) vs. placebo | 0.73 | 0.45-1.20 | 0.22 |
| S-Oxprenolol (20) vs. placebo | 0.47 | 0.28-0.81 | 0.0061 |
| Rilutek vs. S-Oxprenolol (10) | 1.13 | 0.59-2.14 | 0.14 |
| Rilutek vs. S-Oxprenolol (20) | 1.96 | 0.94-4.08 | 0.072 |
| Propanolol vs. S-Oxprenolol (10) | 0.92 | 0.53-1.57 | 0.75 |
| Propanolol vs. S-Oxprenolol (20) | 1.67 | 0.91-3.06 | 0.099 |
| R-Oxprenolol (10) vs. S-Oxprenolol (10) | 0.78 | 0.45-1.36 | 0.17 |
| S-Oxprenolol (20) vs. S-Oxprenolol (20) | 1.48 | 0.79-2.75 | 0.22 |

Example 10

Effects of S-Oxprenolol Compared to R-Oxprenolol and Rilutek

To study the effect of S-oxprenolol on body weight, body weight was monitored over time. FIG. 20A-20C show the change of body weight in mice administered S-oxprenolol at a dosage of 20 mg/kg/day or 10 mg/kg/day; R-oxprenolol at a dosage of 20 mg/kg/day; rilutek at a dosage of 30 mg/kg/day; or placebo. FIG. 20A shows results for all mice. FIG. 20B shows results for male mice. FIG. 20C shows results for female mice. The number of all mice in the population is indicated as "n" in at the bottom of FIGS. 20A-20C.

To study the effect of the test compounds on lean body mass, lean mass was determined at the end of the study. In this experiment, all mice were killed using the 30 seconds endpoint and hence all mice were equally diseased at the end of the study. FIGS. 20D-20F show the change in lean body mass (in grams) of mice that were administered S-oxprenolol at a dosage of 20 mg/kg/day or 10 mg/kg/day; R-oxprenolol at a dosage of 20 mg/kg/day; rilutek at a dosage of 30 mg/kg/day; or placebo. FIG. 20D shows results for all mice. FIG. 20E shows results for male mice. FIG. 20F shows results for female mice. The number of all mice in the population is indicated as "n" in at the bottom of FIGS. 20D-20F.

To study the effect of the test compounds on fat mass, the fat mass were determined at the end of the study. FIGS. 20G-20I show the change in fat mass (in grams) of mice administered S-oxprenolol at a dosage of 20 mg/kg/day or 10 mg/kg/day; R-oxprenolol at a dosage of 20 mg/kg/day; rilutek at a dosage of 30 mg/kg/day; or placebo. FIG. 20G shows results for all mice. FIG. 20H shows results for male mice. FIG. 20I shows results for female mice. The number of all mice in the population is indicated as "n" in at the bottom of FIGS. 20G-20I.

FIGS. 21A-21C show results for heart weight at the end of the study. FIGS. 21A-21C show the heart weight (in milligrams) of mice administered S-oxprenolol at a dosage of 20 mg/kg/day or 10 mg/kg/day; R-oxprenolol at a dosage of 20 mg/kg/day; rilutek at a dosage of 30 mg/kg/day; or placebo. FIG. 21A shows results for all mice. FIG. 21B shows results for male mice. FIG. 21C shows results for female mice. The number of all mice in the population is indicated as "n" in at the bottom of FIGS. 21A-21C.

FIGS. 21D-21F show results for gastrocnemius muscle weight at the end of the study. FIGS. 21D-21F show the gastrocnemius muscle weight (in milligrams) of mice administered S-oxprenolol at a dosage of 20 mg/kg/day or 10 mg./kg/day; R-oxprenolol at a dosage of 20 mg/kg/day; rilutek at a dosage of 30 mg/kg/day; or placebo. FIG. 21D shows results for all mice. FIG. 21E shows results for male mice. FIG. 21F shows results for female mice. The number of all mice in the population is indicated as "n" in at the bottom of FIGS. 20D-20F.

FIGS. 21G-21I show results for tibialis muscle weight at the end of the study. FIGS. 21G-21I show the tibialis muscle weight (in milligrams) of mice administered S-oxprenolol at a dosage of 20 mg/kg/day or 10 mg/kg/day; R-oxprenolol at a dosage of 20 mg/kg/day; rilutek at a dosage of 30 mg/kg/day; or placebo. FIG. 21G shows results for all mice. FIG. 21H shows results for male mice. FIG. 21I shows results for female mice. The number of all mice in the population is indicated as "n" in at the bottom of FIGS. 21G-21I.

The following tables show results for mice administered with S-oxprenolol at a dosage of 20 mg/kg/day or 10 mg/kg/day; R-oxprenolol at a dosage of 20 mg/kg/day or 10 mg/kg/day; rilutek at a dosage of 30 mg/kg/day; propanolol at a dosage of 10 mg/kg/day; oxprenolol (racemic) at a dosage of 20 mg/kg/day; or placebo. The results for delta body weight, delta lean mass, delta fat mass, average delta body weight, average delta lean mass, average delta fat mass, heart mass, gastrocnemius mass, soleus mass, EDL, and BAT were obtained with tests according the examples herein.

TABLE 7

Data for all mice administered with S-oxprenolol, R-oxprenolol, rilutek, propanolol, oxprenolol (racemic), or placebo.

| | placebo | 30 mg/kg/d rilutek | 10 mg/kg/d propanolol | 20 mg/kg/d oxprenolol |
|---|---|---|---|---|
| Δ body weight [g] | −5.51 ± 0.34 | −5.10 ± 0.35 | −5.89 ± 0.42 | −5.59 ± 0.48 |
| Δ lean mass [g] | −4.31 ± 0.26 | −3.71 ± 0.27* | −4.89 ± −0.26 | −4.67 ± 0.42 |
| Δ fat mass [g] | −1.64 ± 0.15 | −1.91 ± 0.15 | −1.82 ± 0.25 | −1.49 ± 0.12 |
| Average Δ body weight [mg/day] | −153.7 ± 22.2 | −121.6 ± 15.2 | −127.6 ± 10.6 | −123.6 ± 1.2.3 |
| Average Δ lean mass [mg/day] | −135.9 ± 19.5 | −92.31 ± 15.84 | −107.0 ± 7.4 | −102.0 ± 10.7 |
| Average Δ fat mass [mg/day] | −35.6 ± 3.8 | −50.1 ± 6.1* | −43.9 ± 5.5 | −33.1 ± 2.6 |
| Heart [mg] | 100.5 ± 3.4 | 103.5 ± 2.8 | 104.0 ± 3.2 | 100.2 ± 3.2 |
| gastrocnemius [mg] | 47.7 ± 3.0 | 55.2 ± 3.0 | 52.4 ± 3.3 | 52.2 ± 2.3 |
| soleus [mg] | 5.85 ± .022 | 5.47 ± 0.39 | 5.60 ± 0.28 | 4.99 ± 0.36* |
| EDL [mg] | 6.94 ± 0.25 | 6.71 ± 0.32 | 7.11 ± 0.37 | 7.24 ± 0.41 |
| BAT [mg] | 41.2 ± 2.4 | 53.7 ± 2.9** | 45.1 ± 2.9 | 40.6 ± 2.8 |

| | 10 mg/kg/d R-oxprenolol | 20 mg/kg/d R-oxprenolol | 10 mg/kg/d S-oxprenolol | 20 mg/kg/d S-oxprenolol |
|---|---|---|---|---|
| Δ body weight [g] | −6.36 ± 0.39 | −5.21 ± 0.39 | −5.4 ± 0.43 | −5.56 ± 0.47 |
| Δ lean mass [g] | −5.11 ± 0.32 | −4.60 ± 0.28 | −3.31 ± 0.33*#### | −4.78 ± 0.41 |
| Δ fat mass [g] | −1.71 ± 0.15 | −1.59 ± 0.15 | −1.26 ± 0.14 | −1.56 ± 0.18 |
| Average Δ body weight [mg/day] | −146.1 ± 11.1 | −111.0 ± 9.4 | −123 ± 11.6 | $-99.4 ± 9.7^{p-0.064}$ |
| Average Δ lean mass [mg/day] | −125.8 ± −12.7 | −96.6 ± 6.4 | −89.6 ± 9.1* | −93.3 ± 7.5* |
| Average Δ fat mass [mg/day] | −38.3 ± 4.2 | −32.6 ± 3.0 | −29.4 ± 3.7 | −29.8 ± 3.6 |
| Heart [mg] | 101.2 ± 2.7 | 100.7 ± 3.8 | 108.6 ± 5.8 | 104.1 ± 3.5 |
| gastrocnemius [mg] | 50.8 ± 3.3 | 47.0 ± 2.6 | 55.1 ± 4.0 | 50.1 ± 2.9 |
| soleus [mg] | 4.49 ± 0.36** | 5.49 ± 0.34 | 5.89 ± 0.35 | 6.42 ± 0.39 |
| EDL [mg] | 6.53 ± 0.47 | 5.89 ± 0.31* | 7.18 ± 0.34 | 7.791 ± 0.29*+++ |
| BAT [mg] | 44.5 ± 3.4 | 43.3 ± 4.1 | 46.8 ± 3.5 | 43.7 ± 2.3 |

Δ: delta, average

Δ [mg/day]: average delta per day alive after disease onset,

EDL: extensor digitorum longus,

BAT: brown adipose tissue,

*: $p < 0.05$,

**: $p < 0.01$ vs placebo,

: $p < 0.001$ vs 10 mg/kg/d propanolol, $: $p < 0.05$ vs 20 mg/kg/d R-oxprenolol, +++: $p < 0.001$ vs 30 mg/kg/d rilutek

TABLE 8

Data for male mice administered with S-oxprenolol, R-oxprenolol, rilutek, propanolol, oxprenolol (racemic), or placebo.

| | placebo | 30 mg/kg/d rilutek | 10 mg/kg/d propanolol | 20 mg/kg/d oxprenolol |
|---|---|---|---|---|
| Δ body weight [g] | −6.81 ± 0.54 | −5.91 ± 0.43 | −6.11 ± 0.54 | −5.94 ± 0.77 |
| Δ lean mass [g] | −5.44 ± 0.39 | −4.19 ± 0.38* | −5.06 ± 0.37 | −5.64 ± 0.68 |
| Δ fat mass [g] | −1.66 ± 0.27 | −2.09 ± 0.22 | −1.99 ± 0.26 | −1.33 ± 0.13 |
| Average Δ body weight [mg/day] | −215.8 ± 36.4 | −120.4 ± 17.9* | −142.7 ± 15.9 | −124.8 ± 20.7 |
| Average Δ lean mass [mg/day] | −178.1 ± 31.9 | −87.4 ± 21.1* | −118.6 ± 10.6 | −119.4 ± 17.7 |
| Average Δ fat mass [mg/day] | −40.5 ± 6.8 | −57.5 ± 11.3 | −51.9 ± 6.9 | −28.3 ± 3.1 |
| Heart [mg] | 117.9 ± 3.4 | 115.6 ± 2.4 | 113.5 ± 4.6 | 110.2 ± 2.9 |
| gastrocnemius [mg] | 57.1 ± 5.3 | 58.3 ± 4.9 | 63.3 ± 3.6 | 54.7 ± 3.9 |
| soleus [mg] | 6.03 ± 0.32 | 5.72 ± 0.64 | 5.63 ± 0.38 | 5.21 ± 0.51 |
| EDL [mg] | 7.83 ± 0.32 | 7.20 ± 0.51 | 7.94 ± 0.55 | 7.49 ± 0.72 |
| BAT [mg] | 44.9 ± 3.9 | 54.8 ± 3.9 | 48.7 ± 5.1 | 45.7 ± 3.6 |

TABLE 8-continued

Data for male mice administered with S-oxprenolol, R-oxprenolol, rilutek, propanolol, oxprenolol (racemic), or placebo.

|  | 10 mg/kg/d R-oxprenolol | 20 mg/kg/d R-oxprenolol | 10 mg/kg/d S-oxprenolol | 20 mg/kg/d S-oxprenolol |
|---|---|---|---|---|
| Δ body weight [g] | −6.515 ± 0.65 | −5.53 ± 0.57 | −6.57 ± 0.57 | −6.36 ± 0.67 |
| Δ lean mass [g] | −5.55 ± 0.47 | −5.12 ± 0.38 | −3.67 ± 0.49**# | −5.34 ± 0.56 |
| Δ fat mass [g] | −1.57 ± 0.21 | −1.48 ± 0.16 | −1.44 ± 0.19 | −1.78 ± 0.28 |
| Average Δ body weight [mg/day] | −153.5 ± 16.1 | −116.0 ± 13.7* | −150.3 ± 14.5 | −115.7 ± 12.6* |
| Average Δ lean mass [mg/day] | −129.7 ± 9.9 | −106.4 ± 8.5 | −115.1 ± 13.9 | −95.8 ± 10.6* |
| Average Δ fat mass [mg/day] | −37.4 ± 6.4 | −29.9 ± 3.5 | −33.6 ± 5.7 | −32.1 ± 5.4 |
| Heart [mg] | 107.4 ± 3.4* | 112.0 ± 4.1 | 122.6 ± 8.8 | 112.4 ± 4.5 |
| gastrocnemius [mg] | 53.8 ± 5.1 | 49.9 ± 3.0 | 59.1 ± 6.6 | 53.1 ± 4.3 |
| soleus [mg] | 4.74 ± 0.51* | 5.84 ± 0.45 | 6.04 ± 0.53 | 6.58 ± 0.61 |
| EDL [mg] | 6.59 ± 0.61 | 5.81 ± 0.42*** | 7.28 ± 0.47 | 8.15 ± 0.39$$$ |
| BAT [mg] | 46.7 ± 4.9 | 53.9 ± 6.8 | 53.2 ± 5.0 | 46.5 ± 3.0 |

Δ: delta, average
Δ [mg/day]: average delta per day alive after disease onset,
EDL: extensor digitorum longus,
BAT: brown adipose tissue,
*: $p < 0.05$,
**: $p < 0.01$,
***: $p < 0.001$ vs placebo,
: $p < 0.05$ vs 10 mg/kg/d propanolol,
$$$: $p < 0.001$ vs 20 mg/kg/d R-oxprenolol

TABLE 9

Data for female mice administered with S-oxprenolol, R-oxprenolol, rilutek, propanolol, oxprenolol (racemic), or placebo.

|  | placebo | 30 mg/kg/d rilutek | 10 mg/kg/d propanolol | 20 mg/kg/d oxprenolol |
|---|---|---|---|---|
| Δ body weight [g] | −4-55 ± 0.32 | −4.49 ± 0.46 | −5.66 ± 0.66 | −5.27 ± 0.61 |
| Δ lean mass [g] | −3.42 ± 0.25 | −3.31 ± 0.37 | −4.70 ± 0.37** | −3.76 ± 0.42 |
| Δ fat mass [g] | −1.61 ± 0.15 | −1.76 ± 0.21 | −1.65 ± 0.44 | −1.64 ± 0.21 |
| Average Δ body weight [mg/day] | −97.3 ± 20.6 | −122.9 ± 25.7 | −111.3 ± 13.2 | −122.5 ± 14.7 |
| Average Δ lean mass [mg/day] | −84.3 ± 11.9 | −96.9 ± 24.2 | −91.2 ± 8.3 | −85.8 ± 11.6 |
| Average Δ fat mass [mg/day] | −33.2 ± 4.6 | −42.2 ± 6.1 | −30.9 ± 8.3 | −37.5 ± 3.7 |
| Heart [mg] | 86.1 ± 1.5 | 91.4 ± 2.3 | 93.8 ± 2.7* | 89.5 ± 2.4 |
| gastrocnemius [mg] | 21.2 ± 2.9 | 54.1 ± 3.8** | 40.6 ± 3.3 | 49.5 ± 2.1 |
| soleus [mg] | 5.72 ± 0.30 | 5.26 ± 0.48 | 5.57 ± 0.43 | 4.76 ± 0.52 |
| EDL [mg] | 6.29 ± 0.28 | 6.28 ± 039 | 6.21 ± 0.37 | 6.97 ± 0.36 |
| BAT [mg] | 38.8 ± 2.9 | 53.7 ± 4.5* | 41.2 ± 2.2 | 35.2 ± 4.1 |

|  | 10 mg/kg/d R-oxprenolol | 20 mg/kg/d R-oxprenolol | 10 mg/kg/d S-oxprenolol | 20 mg/kg/d S-oxprenolol |
|---|---|---|---|---|
| Δ body weight [g] | −6.19 ± 0.42 | −4.85 ± 0.55 | −4.51 ± 0.55 | −4.57 ± 0.55 |
| Δ lean mass [g] | −3.76 ± 0.41* | −4.55 ± 0.37 | −3.99 ± 0.37## | −3.97 ± 0.49 |
| Δ fat mass [g] | −1.87 ± 0.22 | −1.71 ± 0.26 | −1.17 ± 0.21$^{p=0.059}$ | −1.29 ± 0.17 |
| Average Δ body weight [mg/day] | −137.4 ± 15.5 | −105.2 ± 13.1 | −103.3 ± 16.1 | −82.0 ± 13.6 |
| Average Δ lean mass [mg/day] | −121.3 ± 25.7 | −85.2 ± 9.1 | −69.2 ± 10.8 | 90.7 ± 10.9 |
| Average Δ fat mass [mg/day] | −41.4 ± 5.3 | −35.6 ± 5.0 | −25.9 ± 4.8 | −26.8 ± 4.4+ |
| Heart [mg] | 94.4 ± 3.4* | 88.5 ± 4.6 | 92.3 ± 3.2$^{p=0.064}$ | 92.8 ± 3.0* |
| gastrocnemius [mg] | 47.5 ± 4.1 | 43.6 ± 4.2 | 50.5 ± 4.0*$^{p=0.060 vs propanolol}$ | 46.2 ± 3.9 |

TABLE 9-continued

Data for female mice administered with S-oxprenolol, R-oxprenolol, rilutek, propanolol, oxprenolol (racemic), or placebo.

| soleus [mg] | 4.23 ± 0.51* | 5.09 ± 0.52 | 5.71 ± 0.48 | 6.15 ± 0.30 |
| --- | --- | --- | --- | --- |
| EDL [mg] | 6.45 ± 0.75 | 5.98 ± 0.47 | 7.03 ± 0.51 | 7.29 ± 0.42*$ |
| BAT [mg] | 42.1 ± 4.6 | 32.6 ± 1.9 | 39.4 ± 4.2 | 37.1 ± 2.9 |

Δ: delta, average
Δ [mg/day]: average delta per day alive after disease onset,
EDL: extensor digitonim longus,
BAT: brown adipose tissue,
*: $p < 0.05$,
**: $p < 0.01$,
***: $p < 0.001$ vs placebo,
: $p < 0.01$ vs 10 mg/kg/d propanolol,
$: $p < 0.05$ vs 20 mg/kg/d R-oxprenolol,
†: $p < 0.05$ vs 30 mg/kg/d rilutek

The invention claimed is:

1. A method of increasing locomotive activity in an individual having amyotrophic lateral sclerosis, comprising administering to the individual an effective amount of a composition comprising a beta blocker which is oxprenolol or a pharmaceutically acceptable salt thereof, wherein the composition is enantiomerically enriched for the S-enantiomer of the beta-blocker, wherein the composition comprises an enantiomeric excess of at least about 50% of S-oxprenolol.

2. The method of claim 1, wherein the composition comprises an enantiomeric excess of at least about 80% of S-oxprenolol.

3. The method of claim 2, wherein the composition comprises an enantiomeric excess of at least about 99% of S-oxprenolol.

4. The method of claim 3, wherein the composition comprises an enantiomeric excess of at least about 99% of S-oxprenolol.

5. The method of claim 1, wherein the amyotrophic lateral sclerosis is sporadic amyotrophic lateral sclerosis.

6. The method of claim 1, wherein the amyotrophic lateral sclerosis is familial amyotrophic lateral sclerosis.

7. The method of claim 1, wherein the amyotrophic lateral sclerosis is Western Pacific amyotrophic lateral sclerosis.

8. The method of claim 1, wherein the amyotrophic lateral sclerosis is juvenile amyotrophic lateral sclerosis.

9. The method of claim 1, wherein the amyotrophic lateral sclerosis is Hiramaya Disease.

10. The method of claim 1, wherein the amyotrophic lateral sclerosis is progressive bulbar palsy (PBP), progressive muscular atrophy (PMA), primary lateral sclerosis (PLS), or ALS with multi-system involvement.

11. The method of claim 1, wherein the composition is administered orally.

12. The method of claim 1, wherein the amount of S-oxprenolol in the composition is about 80 to about 160 mg daily.

13. The method of claim 1, wherein the composition is administered daily or twice daily.

* * * * *